(12) United States Patent
Hsiao et al.

(10) Patent No.: US 8,519,007 B2
(45) Date of Patent: Aug. 27, 2013

(54) USE CERTAIN DITERPENE COMPOUNDS IN THE TREATMENT OF ANDROGEN RECEPTOR-ASSOCIATED DISEASES

(75) Inventors: Pei-Wen Hsiao, Taipei (TW); Feng-Min Lin, Niaosong Township, Kaohsiung County (TW); Sheng-Yang Wang, Sindian (TW)

(73) Assignee: Academia Sinica, Taipei (TW)

( * ) Notice: Subject to any disclaimer, the term of this patent is extended or adjusted under 35 U.S.C. 154(b) by 720 days.

(21) Appl. No.: 12/508,832

(22) Filed: Jul. 24, 2009

(65) Prior Publication Data
US 2010/0022632 A1    Jan. 28, 2010

Related U.S. Application Data

(60) Provisional application No. 61/129,875, filed on Jul. 25, 2008.

(51) Int. Cl.
*A61K 31/12* (2006.01)

(52) U.S. Cl.
USPC .......................................................... 514/680

(58) Field of Classification Search
USPC .......................................................... 514/680
See application file for complete search history.

(56) References Cited

PUBLICATIONS

Tu et al., Plant Med., 2007;73:1407-1409.*
Singh et al., Endocrine-Related Cancer, 2006;13:653-666.*
M. Bispo de Jesus et al. "Ferruginol Suppresses Survival Signaling Pathways in Androgen-Independent Human Prostate Cancer Cells," Biochimie 90, pp. 843-854 (2008).
K.-P. Chao, et al., "Anti-inflammatory Activity of Sugiol, A Diterpene Isolated from *Calocedrus formosana* Bark," Planta Med 71, pp. 300-305 (2005).
I. Córdova et al., "Synthesis and antiproliferative activity of novel sugiol β-amino alcohol analogs," European Journal of Medicinal Chemistry 41, pp. 1327-1332 (2006).
M. Iwamoto et al., "Potential Antitumor Promoting Diterpenoids from the Stem Bark of *Thuja standishii*," Planta Med 69, pp. 69-72 (2003).
P. Li et al., "Optimizing Ultraperformance Liquid Chromatographic Analysis of 10 Diterpenoid Compounds in *Salvia miltiorrhiza* Using Central Composite Design," Journal of Agricultural and Food Chemistry 56, pp. 1164-1171 (2008).
F.-M. Lin et al., "A Novel Diterpene Suppresses CWR22Rv1 Tumor Growth in vivo through Antiproliferation and Proapoptosis," Cancer Research 68, pp. 6634-6646 (2008), and Supplementary data for this article (4 pages) from http://cancerres.aacrjournals.org.
F.-M. Lin, et al., "Compounds From *Wedelia chinesis* Synergistically Suppress Androgen Activity and Growth in Prostate Cancer Cells," Carcinogensis 28, No. 12, pp. 2521-2529 (2007).
K.-H. Son, et al., "Anti-tumor abietane diterpenes from the cones of *Sequoia sempervirens*," Biorganic & Medicinal Chemistry Letters 15, pp. 2019-2021 (2005).

(Continued)

*Primary Examiner* — San-Ming Hui
(74) *Attorney, Agent, or Firm* — Finnegan, Henderson, Farabow, Garrett & Dunner LLP

(57) ABSTRACT

The present invention discloses certain diterpenes that can be used to inhibit androgen receptor activity, induce apoptosis and block cell cycle progression of androgen receptor-dependent cells. Androgen receptor has been associated with various diseases such as prostate cancer, androgeneic alopecia, breast cancer, acne etc. Accordingly, the present invention further discloses methods of treating androgen receptor-associated diseases by administering the disclosed diterpenes.

12 Claims, 25 Drawing Sheets

(56) References Cited

PUBLICATIONS

M. Takei, et al., "Diterpenes Inhibit IL-12 Production by DC and Enhance Th2 Cells Polarizataion," Biochemcial and Biophysical Research Communications 355, pp. 603-610 (2007).

M. Takei, et al., "Dipterpene, 16-phyllocladanol Enhances Th1 Polarization Induced by LPS-primed DC, but not TNF-α-Primed DC," Biochemical and Biophysical Research communications 370, pp. 6-10, (2008).

W.-C. Tu et al., "Diterpenes from *Cryptomeria japonica* Inhibit Androgen Receptor Transcriptional Activity in Prostate Cancer Cells," Planta Med 73, pp. 1407-1409 (2007).

* cited by examiner

A

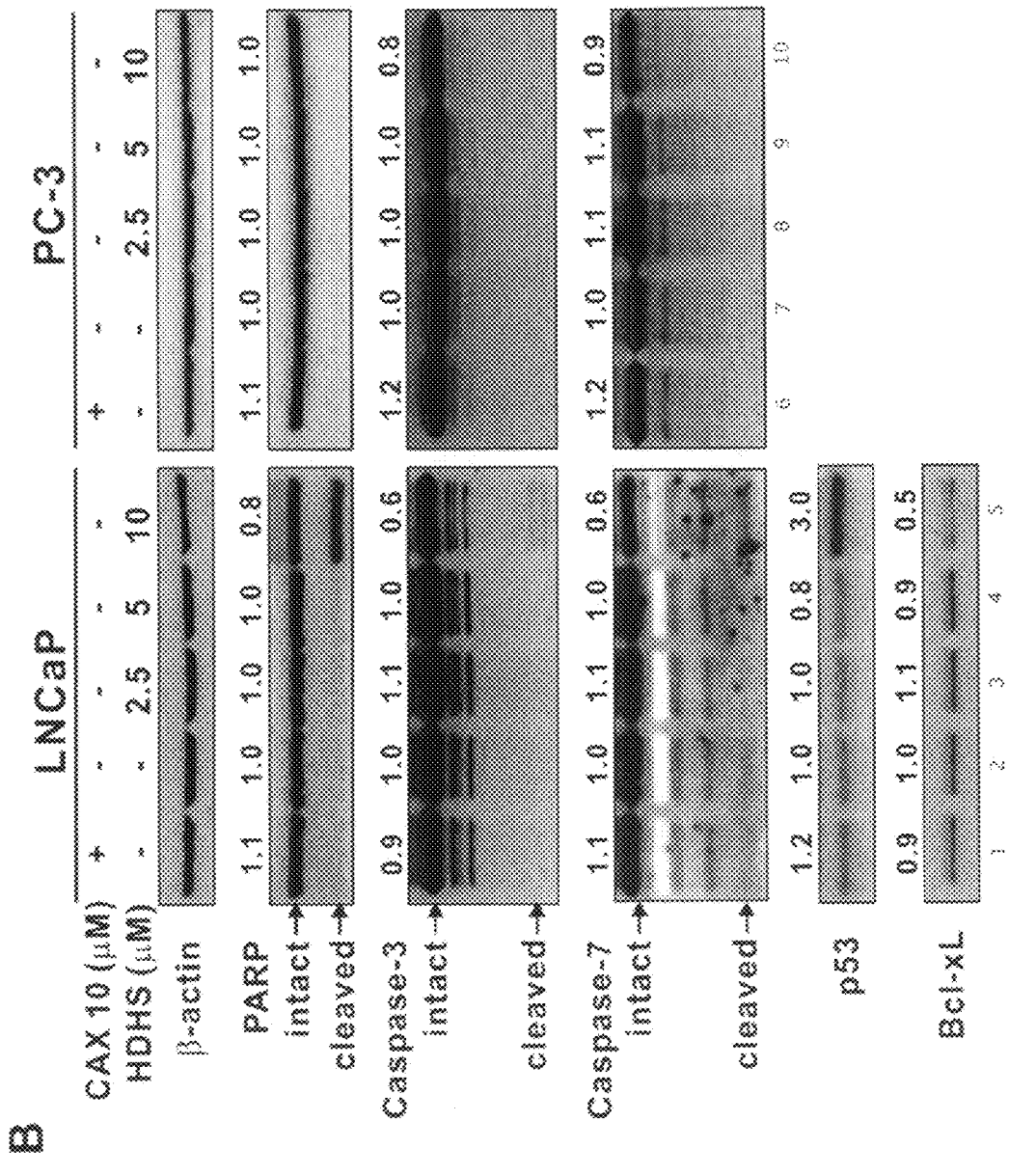

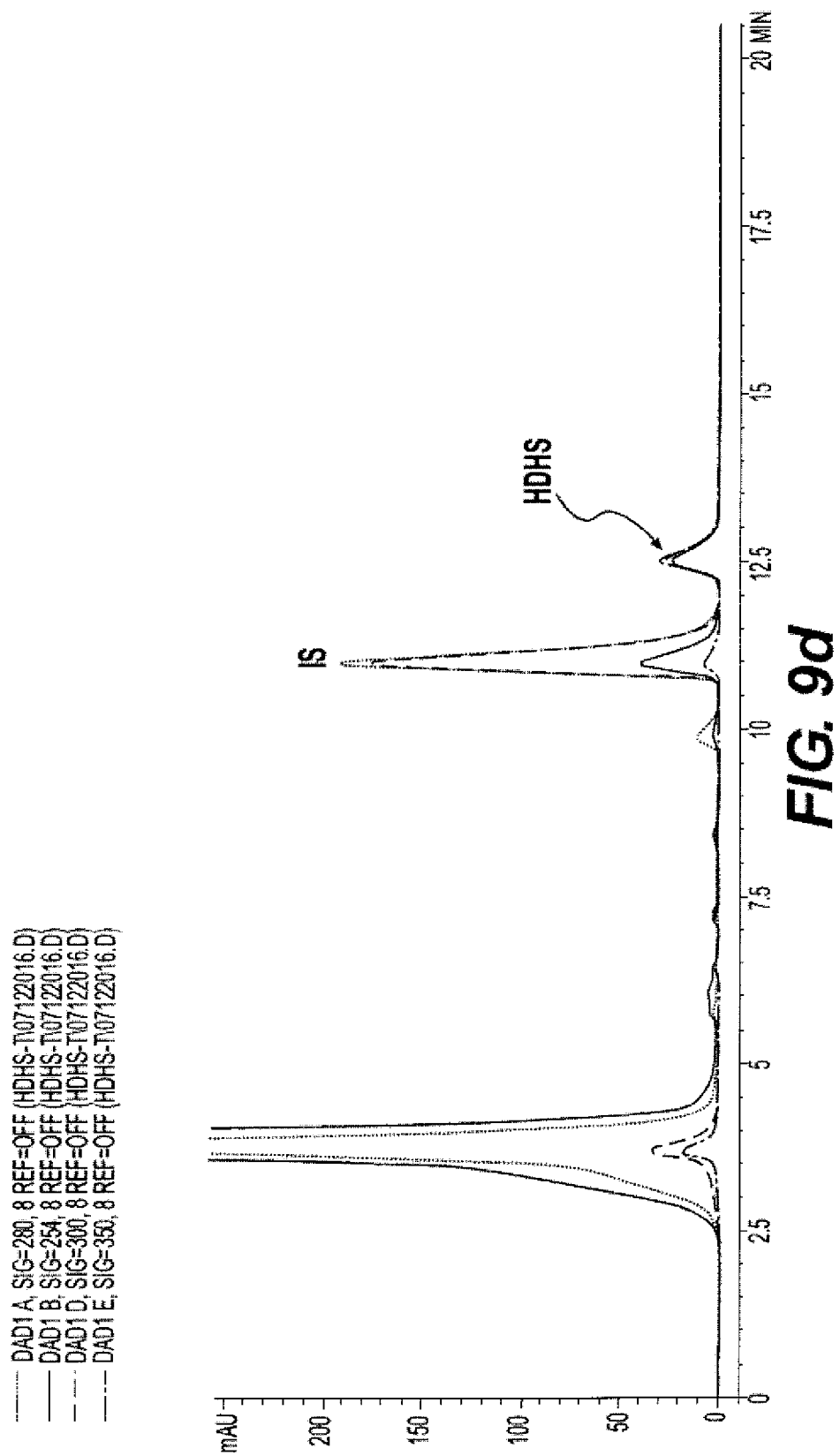

USE CERTAIN DITERPENE COMPOUNDS IN THE TREATMENT OF ANDROGEN RECEPTOR-ASSOCIATED DISEASES

This application claims benefit of priority under 35 U.S.C. §119 to the U.S. provisional patent application No. 61/129,875, filed Jul. 25, 2008, the entire contents of which are incorporated herein by reference.

FIELD OF THE INVENTION

This invention relates to the use of certain types of diterpene compounds for inhibiting activities of androgen receptors and methods of using those compounds for treatment of androgen receptor-associated diseases, including prostate cancer, benign prostate hypertrophy, bladder cancer, breast cancer, polycystic ovary syndrome (PCOS), androgenic alopecia, hirsutism, acne, oily skin, seborrhea, and hidradenitis suppurativa.

BACKGROUND OF THE INVENTION

Androgens have been associated with the progression of many diseases such as prostate cancer, benign prostate hypertrophy, male alopecia, acne, and breast cancer, etc. Androgens execute their functions through binding to the androgen receptor (AR) that then regulates gene transcription in the cell nucleus. AR receptor is a member of the nuclear receptor superfamily that acts as a ligand-dependant transcription factor. AR is expressed mainly in androgen target tissue such as prostate, skeletal muscle, liver, skin and CNS, with the highest expression observed in the prostate. At the cellular level, unbound AR is located mainly in the cytoplasm where it is associated with a complex of heat shock proteins, mainly through interactions with the ligand binding domain (LBD). Upon ligand binding, AR enters the nucleus and activates target genes involved in diverse biological processes such as proliferation, differentiation, apoptosis and secretion. Various AR ligands have been discovered and developed for the treatment of muscle wasting, anemia, benign prostate hyperplasia and prostate cancers (Gao W et al., Drug Discov Today 2007; 12:241-248).

Prostate cancer (PCa) is the most common lethal non-cutaneous malignancy in many Western countries and androgen is one of the major factors influencing PCa development (Hendriksen P J et al., Cancer Res 2006: 66:5012-20). Androgen-AR activity has been tightly associated with the growth, differentiation and even carcinogenesis of the prostate (Culig Z. Urology 2003; 62:21-6; Heinlein C A et al., Endocr Rev 2004; 25:276-308). Furthermore, expression of AR protein is detected in nearly all prostate cancers (PCa) including those of distant metastases and ablation-resistant cases (Shah R B et al., Cancer Res 2004; 64:9209-06). AR also up-regulates the gene transcription of prostate specific antigen (PSA) which is the most widely used serological biomarker of PCa for both diagnosis and therapeutic assessment (Balk SP et al., J Clin Oncol 2003; 21:383-91; Cleutjens K B et al., Mol Endocrinol 1997; 11:148-61). It is understood that signaling pathways mediated by androgens and AR are essential for both normal and malignant prostate cells, although there are differences between these two states of prostate cells (Hendriksen P J et al., Cancer Res 2006; 66:5012-20; Denmeade S R et al., Prostate 1996; 28:251-65). At initial diagnosis, most PCa responds to androgen ablation therapy, which prevents the production or blocks the action of androgens, and inhibits prostate cancer growth (Craft N et al., Cancer Res 1999; 59:5030-6). However, cells eventually become androgen-independent or hormone-resistant, and tumors metastasize as the patient's disease advances. This is likely due to the fact that after the development of hormone resistance, many PCa still express AR, which continues to promote PCa progression. Therefore, targeting AR activity in cancerous prostate cells may be a more effective way for treating prostate cancer as AR is involved at different stages of the disease. In addition, inhibiting AR activity might eventually become beneficial for treating other types of AR-associated diseases such as male alopecia, acne, and breast cancer, etc. Nonetheless, currently existing antiandrogen drugs, such as flutamide, niutamide, and bicalutamide, induce severe side effects and are palliative or ineffective towards terminal prostate cancers Therefore, there is an urgent need to develop or search more effective therapeutic compounds for both prostate cancer and for other diseases associated with AR activity.

It is accordingly an object of the present invention to provide novel methods of inhibiting AR comprising the use of certain types of diterpenes. While the diterpenes disclosed in the present invention have been previously identified, they have been associated with other biological activities such as anti-microbial, anti-proliferative and cytotoxic activities (Chao K P et al., Planta Med 2005; 71:300-305; Iwamoto M et al., Planta Med 2003; 69: 69-72; Politi M et al., Planta Med 2003; 69:468-70) and one of them was reported to have no biological effect (Politi M et al., Planta Med 2003; 69:468-70). Here, these diterpenes are for the first-time reported to suppress AR activity in human PCa cells. Therefore, it is a further object of the present invention to disclose the use of these specific types of diterpene for the treatment of AR-associated diseases.

SUMMARY OF THE INVENTION

The invention encompasses methods of inhibiting AR activity in a patient comprising administering a diterpene to the patient and allowing the diterpene to reduce AR activity, wherein the diterpene is chosen from the following compounds:

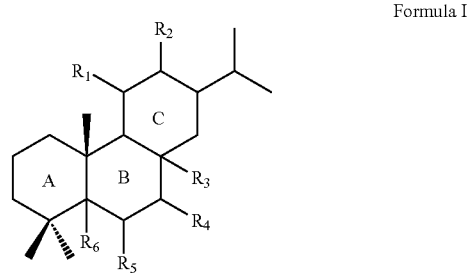

Formula I wherein the rings A, B, and C of the formula I are chosen from cycloalkyl, aryl, and heterocycle, wherein $R_1$ is chosen from H, OH, =O, and $OCH_3$;

$R_2$, $R_4$ and $R_5$ are independently chosen from H, OH, $OCH_3$, =O, $NH_2$, SH, OR, and COOR, wherein R is alkyl or glycosyl;

$R_3$ and $R_6$ are independently chosen from H and OH; and

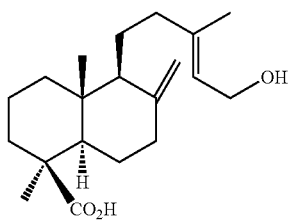

Formula II

The present invention further encompass methods of treating AR-associated diseases comprising administering the diterpene to the patient and allowing the diterpene to reduce androgen receptor activity thereby treating the androgen receptor-associated disease.

In some embodiments, the AR-associated disease is prostate cancer, benign prostate hypertrophy, bladder cancer, breast cancer, polycystic ovary syndrome (PCOS), androgenic alopecia, hirsutism, acne, oily skin, seborrhea, or hidradenitis suppurativa.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIGS. 9A-E. HPLC chromatograms of HDHS extracted from tumor samples. Chromatograms from blank plasma (a), vehicle control group (b), 0.5 mg/kg group (c), 2.5 mg/kg group (d), and tumor samples of (d) spiked with 1000 nmol/g HDHS (e).

DESCRIPTION OF THE EMBODIMENTS

Figure 1:
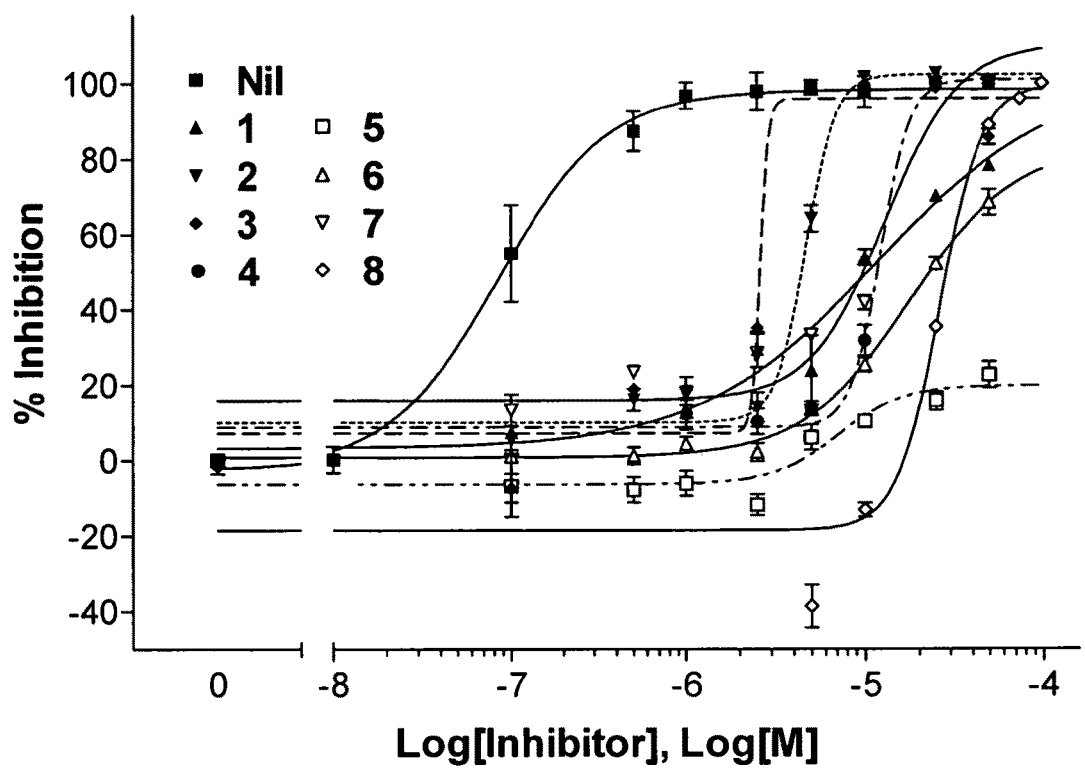
FIG. 1. Dose-response curves of anti-androgen (nilutamide, a positive control) and diterpenes (Compounds 1 to 8) isolated from C. japonica in inhibiting AR.

Reference will now be made in detail to the present embodiments of the invention, examples of which are illustrated in the accompanying drawings. Wherever possible, the same reference numbers will be used throughout the drawings to refer to the same or like parts.

I. Diterpenes of the Invention

A. Chemical Structure

Diterpenes are a class of compounds of formula C20H32. The present invention involves diterpenes selected from the following two formulae:

Formula I

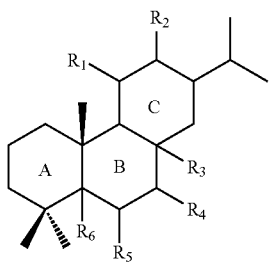

wherein the rings A, B, and C of the formula I are chosen from cycloalkyl, aryl, and heterocycle; wherein $R_1$ is chosen from H, OH, =O, and $OCH_3$;

$R_2$, $R_4$, and $R_5$ are independently chosen from H, OH, $OCH_3$, =O, $NH_2$, SH, OR, and COOR, wherein R is alkyl or glycosyl;

$R_3$ and $R_6$ are independently chosen from H and OH; and

Formula II

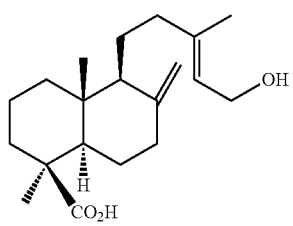

Compounds having Formula I are generally categorized as a abietane-type diterpenes because they share the general formula of an abietane. Specific examples of abietane-type diterpenes that are useful for the present invention include:

Compound 1: cryptojaponol

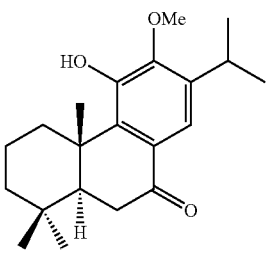

Compound 2: 6, 12-dihydroxyabieta-5,8,11,13-tetraen-7-one, (also called 6 hydroxy-5,6,-dehyrosugiol, "HDHS").

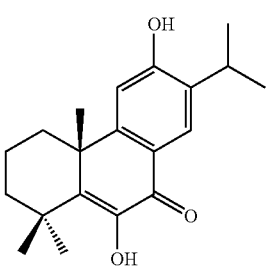

Compound 3: Sugiol.

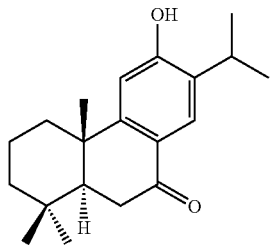

Compound 4: Ferruginol

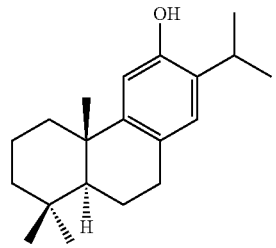

Compound 5: Cupresol.

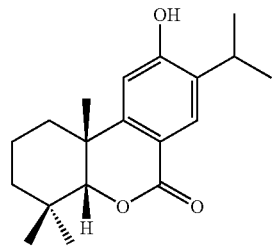

Compound 6: 8-β-hydroxyabieta-9(11),13-dien-12-one.

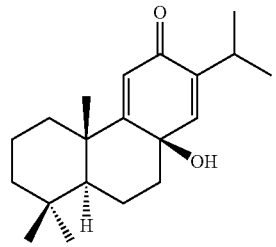

Compound 7: 5-epixanthoperol.

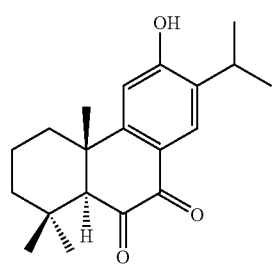

Formula II (or Compound 8 in the present disclosure) is a isocupressic acid that has a labdane skeleton.

B. Methods of Making

Diterpenes are widely-distributed, naturally-occurring secondary metabolites in plants. The diterpenes disclosed in the present invention can be extracted from species like *Cryptomeria japonica*, *Taiwania cryptomerioides, Hayata*, Cupressaceae, *Chamaecyparis formosensis Matsum*, *Chamaecyparis obtusa* var. *formosana*, and *Juniperus formosana Hayata*.

For example, Compounds 1-7 can be purified from a hexane extract of bark of *C. japonica*, and compound 8 (Formula II) can be purified from an ethyl acetate extract of leaves of *C. japonica*.

Various extraction methods can be employed to obtain diterpenes, and such methods are known to the field of natural product isolation. For instance, diterpenes can be isolated from natural resources by methanol or ethanol extraction followed by liquid-liquid partition with ethyl acetate. In this case, diterpenes are likely to be retained in the ethyl acetate layer.

Alternatively, the diterpenes disclosed in the present invention can be produce by a way of biosynthesis using, for example, plant cell fermentation technology. For instance, a cell line that produces a diterpene of interest can be propagated in aqueous medium in fermentation tanks and the compounds can be extracted directly and then purified.

The diterpenes disclosed in the present invention can also be made by way of total chemical synthesis or hemisynthesis. For instance, the disclosed diterpenes can be synthesized from other diterpene compounds, such as those disclosed herein, using standard organic chemical synthesis methods well known in the art. This strategy is beneficial when it is difficult to obtain the desired diterpene in nature, but related compounds are easier to obtain due to their abundance in nature.

II. Methods of Treatment

A. Diseases

The present invention can be used as a way of inhibiting the activities of AR including acting as an anti-androgen.

The diterpenes disclosed in the present invention display one or more of the following properties for treating androgen receptor-associated diseases: inhibit activity of AR in a concentration-dependent fashion; induce AR nuclear localization; suppress transcriptional activity of AR; induce apoptosis and block cell cycle progression in AR-dependent cells; and reduce proliferation and promote apoptosis of AR-dependent tumors in a concentration-dependent fashion.

The present invention further encompasses methods of treating androgen receptor-associated diseases which include, but are not limited to, prostate cancer, benign prostate hypertrophy, bladder cancer, breast cancer, polycystic ovary syndrome (PCOS), androgenic alopecia, hirsutism, acne, oily skin, seborrhea, hidradenitis suppurativa.

B. Routes of Administration

Administration of the diterpenes disclosed herein can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Thus, the subject compositions can be formulated into preparations in solid, semi-solid, liquid, or gaseous forms, such as tablets, capsules, powders, granules, ointments, solutions, suppositories, injections, inhalants and aerosols. The following methods and excipients are merely exemplary and are in no way limiting.

When a therapeutically effective amount of a diterpene is administered orally, the agent may be in the form of a tablet, capsule, powder, solution or elixir. When administered in tablet form, the pharmaceutical composition of the invention may additionally contain a solid carrier such as a gelatin or an adjuvant. The tablet, capsule and powder can contain from about 5 to 95% binding agent, and in other embodiments from about 25 to 90% binding agent. Examples of binding agents are sucrose, kaolin, glycerin, starch dextrins, sodium alginate, carboxymethylcellulose and ethyl cellulose. Coloring and/or flavoring agents may be present. A coating shell may be employed. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition can further contain physiological saline solution, dextrose or other saccharide solution, or glycols such as ethylene glycol, propylene glycol or polyethylene glycol. When administered in liquid form, the pharmaceutical composition can contain from about 0.5 to 90% by weight of the binding agent, and preferably from about 1 to 50% of the binding agent.

When a therapeutically effective amount of diterpene is administered by intravenous, cutaneous or subcutaneous injection, binding agent can be in the form of a pyrogen-free, parenterally acceptable aqueous solution. The preparation of such parenterally acceptable protein solutions, having due regard to pH, isotonicity, stability, and the like, is within the skill in the art. In some embodiments, a pharmaceutical composition for intravenous, cutaneous, or subcutaneous injection can contain, in addition to binding agent an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical compositions of the present invention can also contain stabilizers, preservatives, buffers, antioxidants, or other additive known to those of skill in the art.

In practicing the methods of treatment or use of the present invention, a therapeutically effective amount of diterpene is administered to a subject, e.g., a mammal such as a human or nonhuman mammal, for example, dogs, cats, pigs, cows, sheep, goats, horses, rats, or mice. As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

C. Pharmaceutical Compositions

The diterpenes disclosed in the present invention may be used as a pharmaceutical composition when combined with a pharmaceutically acceptable carrier. Such a composition may contain, in addition to the diterpenes disclosed herein, various diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier may depend on the route of administration.

The diterpenes can be formulated as compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specifications for the dosage unit forms of the invention are dictated by and directly dependent on the unique characteristics of the active compound and the particular therapeutic effect to be achieved, and the limitations inherent in the art of compounding such an active compound for the treatment of individuals.

The amount of diterpene in the pharmaceutical composition of the present invention may depend upon the nature and severity of the condition being treated, and on the nature of prior treatments that the patient has undergone, as well as the patient's age and sex. Ultimately, the attending physician may decide the amount of active ingredient with which to treat each individual patient. Initially, the attending physician may administer low doses of active ingredient and observe the patient's response. Larger doses of active ingredient may be administered until the optimal therapeutic effect is obtained for the patient, and at that point the dosage is not generally increased further. In addition, the dosage amount useful to treat, prevent, inhibit or alleviate conditions can vary with the severity of the condition to be treated and the route of administration. The dose and dose frequency can also vary according to age, body weight, response and past medical history of the individual human patient. Dosages for non-human patients can be adjusted accordingly by one skilled in the art. It is contemplated that the various pharmaceutical compositions used to practice the methods of the present invention can provide from about 100 ng to about 100 mg diterpene per kg body weight per day. Examples of dosage ranges that can be administered to a subject can be chosen from: 1 µg/kg to 10 mg/kg, 1 µg/kg to 5 mg/kg, 10 µg/kg to 10 mg/kg, 10 µg/kg to 5 mg/kg, 100 µg/kg to 50 mg/kg, 100 µg/kg to 5 mg/kg, 500 µg/kg to 25 mg/kg, 500 µg/kg to 10 mg/kg, 500 µg/kg to 5 mg/kg, and 500 µg/kg to 2.5 mg/kg. For example, the daily dose can be chosen from 0.5 mg to 1000 mg per day, 1 mg to 800 mg per day, 2 mg to 500 mg per day, 10 mg to 50 mg per day, 100 mg to 2 g per day, 40 mg to 2 g per day, 40 mg to 200 mg per day. Specific dosages include all of the endpoints listed above. The duration of therapy using the pharmaceutical composition of the present invention may vary, depending on the severity of the disease being treated and the condition and potential idiosyncratic response of each patient. In some embodiments, it is contemplated that the diterpene is taken orally twice a day for 1 month or until the condition is improved. In some embodiments, the diterpene is administered with other treatments such as irradiation, hormone therapy, chemotherapy and surgery.

Toxicity and therapeutic efficacy of diterpene compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Data obtained from the cell culture assays and animal studies can be used in evaluating a range of dosage for use in humans. The dosage of such compounds may lie within a range of circulating concentrations that include the $ED_{50}$ with little or no toxicity. The dosage may vary within this range depending upon the dosage form employed and the route of administration utilized. The therapeutically effective dose of diterpenes can be estimated initially from cell culture assays. A dose may be formulated in animal models to achieve a circulating plasma concentration range that includes the $IC_{50}$ (i.e., the concentration of the test diterpene compound which achieves a half-maximal inhibition of symptoms) as determined in cell culture. Levels in plasma may be measured, for example, by high performance liquid chromatography. The effects of any particular dosage can be monitored by a suitable bioassay.

D. Combination Therapy

The methods of the present invention can be used individually or in combination with other antiandrogens or other treatments, such as flutamide, bicalutamide, nilutamide, irradiation, heat, hormone therapy, chemotherapy and surgery.

For treating androgen receptor-associated cancer such as prostate cancer or breast cancer, the present invention can be useful in combination with known therapeutic agents and anti-cancer agents. A person skilled in the art would be able to discern which combinations of agents would be useful based on the particular characteristics of the drugs and the cancer involved. Such anti-cancer agents include, but are not limited to, cytostatic/cytotoxic agents, anti-proliferative agents, cell cycle checkpoint inhibitors, angiogenesis inhibitors, monoclonal antibody targeted therapeutic agents, tyrosine kinase inhibitors, serine-threonine kinase inhibitors, histone deacetylase inhibitors, heat shock protein inhibitors, and farnesyl transferase inhibitors. The present invention can be useful in combination with radiation therapy.

Definitions

An "isolated," "purified," "substantially isolated," or "substantially pure" molecule (such as a diterpene) is one that has been manipulated to exist in a higher concentration than in nature. For example, a subject diterpene is isolated, purified, substantially isolated, or substantially purified when at least 50%, 70%, 75%, 80%, 85%, 90%, 91%, 92%, 93%, 94%, 95%, 96%, 97%, 98%, 99% or more of non-subject materials with which it is associated in nature have been removed.

The terms "subject," "individual," "host," and "patient" are used interchangeably herein to refer to a living animal, including human and non-human animals. The subject may be a mammal, such as a human or non-human mammal, for example, dogs, cats, pigs, cows, sheep, goats, horses, rats and mice. The term "subject" does not exclude individuals that are entirely normal with respect to a disease, or normal in all respects.

The term "treatment," as used herein, covers any administration or application of remedies for disease in a mammal, including a human, and includes inhibiting the disease, arresting its development, or relieving the disease, for example, by causing regression, or restoring or repairing a lost, missing, or defective function, or stimulating an inefficient process. The term includes obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. Thus, the invention provides both therapeutic and prophylactic treatments, including (1) preventing the disorder from occurring or recurring in a subject who may be predisposed to the disorder but is not yet symptomatic, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, and/or tumor size.

The term "therapeutically effective amount" means the amount of the subject compound that can elicit a desired response, for example, a biological or medical response of a tissue, system, animal, or human that is sought, for example, by a researcher, veterinarian, medical doctor, or other clinician.

"Disease" refers to any condition, infection, disorder, or syndrome that requires medical intervention or for which medical intervention is desirable. Such medical intervention can include treatment, diagnosis and/or prevention.

"Cancer" is any abnormal cell or tissue growth, for example, a tumor, whether malignant, pre-malignant, or non-malignant. It is characterized by uncontrolled proliferation of cells that may or may not invade the surrounding tissue and, hence, may or may not metastasize to new body sites. For example, prostatic intraepithelial neoplasia is encompassed by this invention. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more than one neoplastic cell type. The term cancer includes lung cancer, colon cancer, breast cancer, prostate cancer, liver cancer, pancreatic cancer, bladder cancer, and oral cancer. Prostate cancer includes prostate intraepithelial neoplasia (PIN), adenocarcinoma of the prostate, and carcinoma of the prostate.

"Optionally" means that the subsequently described event or circumstance may but need not occur, and that the description includes instances where the event or circumstance occurs and instances in which the event or circumstance does not.

"Substituted" means that one or more hydrogen atoms are each independently replaced with the same or different substituent.

The term "cycloalkyl" refers to non-aromatic hydrocarbon ring groups having from 3 to about 8 ring carbon atoms, such as having 6 ring carbon atoms. The ring may be saturated or have one or more carbon-carbon double bonds. Non-limiting examples of cycloalkyl groups include cyclohexyl and cyclohexenyl. Cycloalkyl groups may be substituted or unsubstituted.

The term "aryl" refers to any functional group or substituent derived from a 6-membered carbocyclic aromatic ring. Non-limiting examples of aryl groups include phenyl and benzyl.

The term "heterocycle" refers to a ring structure having at least one atom chosen from oxygen, nitrogen, and sulfur, as part of the ring. The ring structure may be saturated or have one or more double bonds. The ring may also be a simple aromatic ring or a non-aromatic ring. Heterocycle may be substituted or unsubstituted.

The term "alkyl" encompasses straight chains and branched chains having the indicated number of carbon atoms, usually from 1 to 20 carbon atoms, for example 1 to 8 carbon atoms. The term "alkyl" also includes groups having any degree or level of saturation, i.e., groups having exclusively single carbon-carbon bonds, groups having one or more double carbon-carbon bonds, groups having one or more triple carbon-carbon bonds, and groups having mixtures of single, double and triple carbon-carbon bonds. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl and the like.

Other embodiments of the invention will be apparent to those skilled in the art from consideration of the specification and practice of the invention disclosed herein. It is intended that the specification and examples be considered as exemplary only, with a true scope and spirit of the invention being indicated by the claims.

EXAMPLES

Example 1

Isolation of Diterpene from *Cryptomeria japonica*

*C. japonica* trees were collected from Nan-Tou County, Taiwan, during spring 2005. The air-dried leaves (14.1 kg) and bark (40.2 kg) of *C. japonica* were crushed and extracted with 70% ethanol (100 L×2) at room temperature for 7 days. The extract was evaporated in vacuo (Rotavapor R200, BÜCHI, Switzerland) to yield a residue (leaf, 1.0 kg; bark, ~1.2 kg) which was suspended in 20% methanol with water. Then an aliquot of leaf extract (60.9 g) and bark extract (52.4 g) were partitioned sequentially with hexane, ethyl acetate or n-butanol (1000 mL×3, 24 h each). Among all extracts, the ethyl acetate fraction of leaf extract (8.3 g) and the hexane fraction of bark extract (4.9 g) exerted significant inhibition of AR activity and were thus subjected to further investigation.

Compounds 1 to 8, as described above, were purified using semipreparative HPLC (Agilent 1100 series system, Palo Alto, Calif.) on a C18 Cosmosil column (particle size 5 μm, 10 mm I.D.×250 mm, Nacalai Tesque, Kyoto, Japan) with a mobile phase of acetonitrile:methanol:water=15:70:15; flow rate, 3 mL/min. The retention times of compounds 1-8 were 14.5, 12.9, 11.2, 30.2, 6.2, 15.7, 8.2, and 8.5 min, respectively, as detected by UV absorption at 254 nm. The chemical structures were identified by 500 MHz FT-NMR (Bruker BioSpin, Bremen, Germany), in agreement with the published literature (Compound 1: Fraga B M et al., J Agric Food Chem 2005; 53:5200-6; Compound 2: Lin Y T et al., J Cln Chem Soc 1975; 22:331-6; Compound 3: Su W C et al., Phytochemistry 1994; 35:1279-84; Compound 4: Bredenberg J B, Acta Chem Scand 1957; 11:932-935; Compound 5: Su M C et al., Phytochemistry 1996; 41:255-61; Compound 6: Burnell R H et al., Can J Chem 1987; 65:775-81; Compound 7: Bredenberg J B, Acta Chem Scand 1960; 14: 385-90; Compound 8: Gardner D R et al., J Aric Food Chem 1994; 42:756-61). The yields of compounds 1 to 8 were 180.4, 113.0, 109.4, 82.1, 40.3, 18.9, 6.6, and 261.7 mg, respectively, and the purity of each was at least 95%, as determined by analytical HPLC using UV detection and by NMR spectroscopy.

Example 2

Cell Culture

LNCaP, PC-3, and 22Rv1 PCa cell lines were obtained from the ATCC (Manassas, Va.). Normal fibroblast NIH-3T3 cells were kindly provided by Dr. Lie-Fen Shyur but are also available from the ATCC. The 103E cell line was derived from 22Rv1 and contains a stably transfected PSA promoter luciferase reporter, which expresses in an androgen-dependent manner as previously described (Lin F M et al., Carcinogenesis 2007; 28:2521-9). Specifically, PSA-Luc expression could be induced in 103E cells by androgen at physiological concentration (10 nM DHT) and could be blocked by increasing dosage of an anti-androgen such as nilutamide (Nil) or bicalutamide (a clinically used antiandrogen with the brand name CASODEX). LNCaP, 22Rv1 and 103E cells were cultured in RPMI 1640 medium (Invitrogen, Carlsbad, Calif.) supplemented with 10% fetal bovine serum (FBS; Hyclone, Logan, Utah). PC-3 and NIH-3T3 were cultured in DMEM (Hyclone) supplemented with 10% FBS. Cultures were maintained in a humidified incubator at 37° C. in 5% $CO_2$/air.

Example 3

Diterpenes 1 to 8 Inhibit Androgen Receptor Transcriptional Activity in Prostate Cancer Cells To study the ability of diterpene Compounds 1 to 8 to inhibit androgen receptor in prostate cancer cells, 103E cell lines as described in Example 2 were used. Cells were treated with various compounds for a period of 20 h and luciferase activity was measured using a luciferase reporter gene assay system (Promega). Results (FIG. 1) indicated that compounds 2, 3, 4, and 7 completely in inhibited AR activity at concentrations below 25 µM. Compounds 1 and 6 inhibited approximately 70% of AR activity at 50 µM. Compound 5 inhibited less than 20% of AR activity at 50 µM and thus its $IC_{50}$ was not determined (ND). The $IC_{50}$ of compound 8 (the only labdane diterpene reported here) for suppressing AR activity was 22.7 µM, with 87% inhibition observed at a concentration of 50 µM. Statistical analysis in Table 1 showed significant differences between each diterpene compound and the vehicle control group.

TABLE 1

$IC_{50}$ AND $INHIBITION_{MAX}$ OF AR ACTIVITIES OF DITERPENES FROM *CRYPTOMERIA JAPONICA*

| Treatments | $IC_{50}$ (µM)[a] | $Inhibition_{max}$ (%)[b] | Source |
|---|---|---|---|
| Vehicle | ND | 0 ± 3% | |
| Nil[c] | 0.08 | 101 ± 5%** (10 µM) | |
| 1 | 8.62 | 77 ± 2%** (50 µM) | bark |
| 2 | 4.80 | 101 ± 4%** (10 µM) | bark |
| 3 | 2.64 | 100 ± 1%** (25 µM) | bark |
| 4 | 11.99 | 100 ± 1%** (25 µM) | bark |
| 5 | ND | 19 ± 6%* (50 µM) | bark |
| 6 | 17.63 | 68 ± 6%** (50 µM) | bark |
| 7 | 12.90 | 100 ± 1%** (25 µM) | bark |
| 8 | 22.72 | 87 ± 3%** (50 µM) | leaves |

[a]$IC_{50}$ (µM) represents the dose of each indicated treatment that gave 50% of the maximal response. ND, not determined.
[b]$Inhibition_{max}$ (%) represents the maximal inhibition of each indicated treatment. The data are mean ± S.D. from three independent experiments of three replicates. Each compound was compared to the vehicle control by paired t-test.
*$P < 0.05$;
**$P < 0.01$.
[c]Anti-androgen (Nil, nilutamide) as a positive control.

Example 4

Diterpene, 6,12-dihydroxyabiete-5,8,11,13-tetraen-7-one, Suppress Androgen-Induced PSA Expression 6,12-dihydroxyabieta-5,8,11,13-tetraen-7-one (Compound 2 described above, also called 6-Hydroxy-5,6-dehydrosugiol (HDHS)) was dissolved in dimethyl sulfoxide (DMSO, 100 mM) and then serially diluted with absolute ethanol into 1000× stock solutions of working concentrations.

Figure 2:
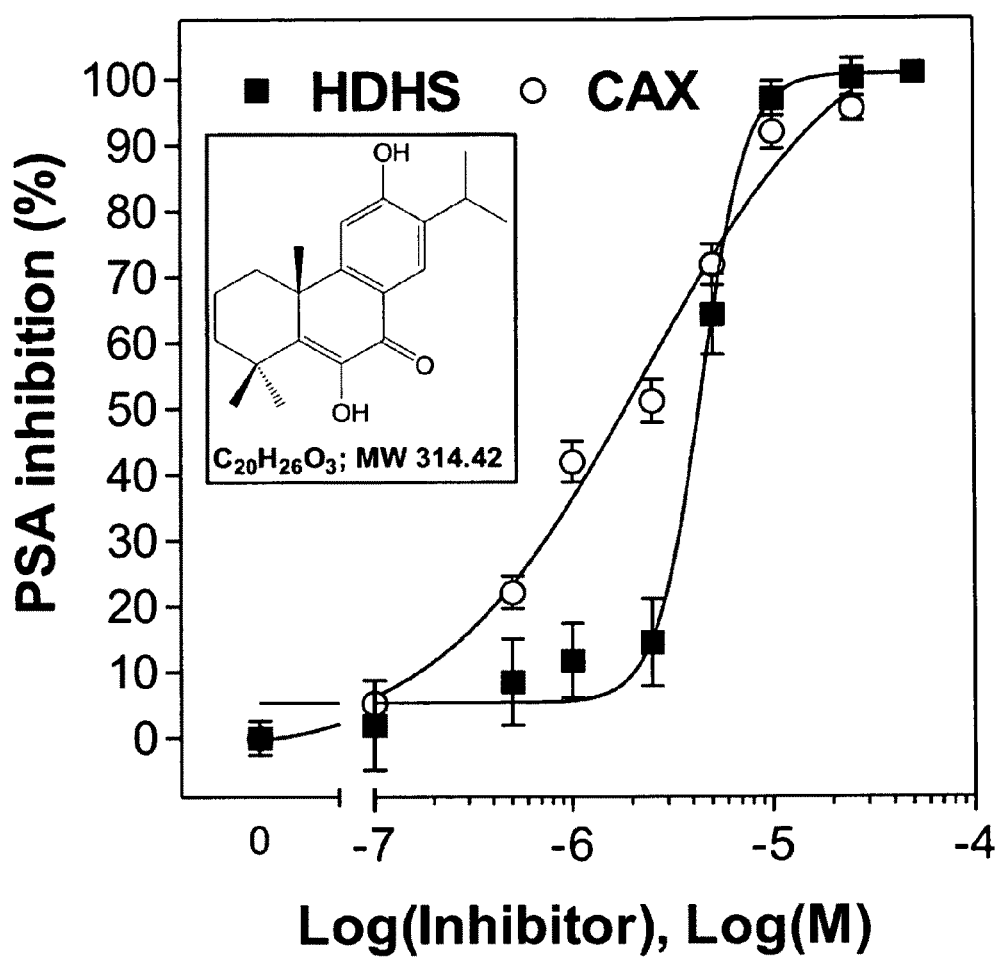
FIGS. 2A-D. Effects of HDHS on AR in PCa cells. A, Dose-response curves of HDHS and CASODEX in inhibiting DHT-induced PSA-luciferase reporter. Inset, chemical structure and molecular formula of HDHS. B, Western blot analysis of LNCaP cells treated with vehicle (Ctrl) or indicated concentrations of HDHS in the presence of 10 n M DHT for 24 h. C, one-hybrid and two-hybrid assays. Left, 22Rv1 cells cotransfected with pG5E1b-Luc, pRL-CMV, and pCMX-GBD-AR(DE) for 24 h and then treated with CASODEX or HDHS in the presence or absence of 10 nM DHT for another 20 h. Right, PC-3 cells cotransfected with pG5E1b-Luc, pRL-CMV, pCMX-GBD-AR(DE), and pCMX-VP16AR(38-918) for 24 h and then treated with CASODEX or HDHS as marked for 20 h. D, Distribution of cellular AR in cells treated with CASODEX or HDHS in the presence or absence of DHT for 1 h. Bar=20 µm.
Figure 2:
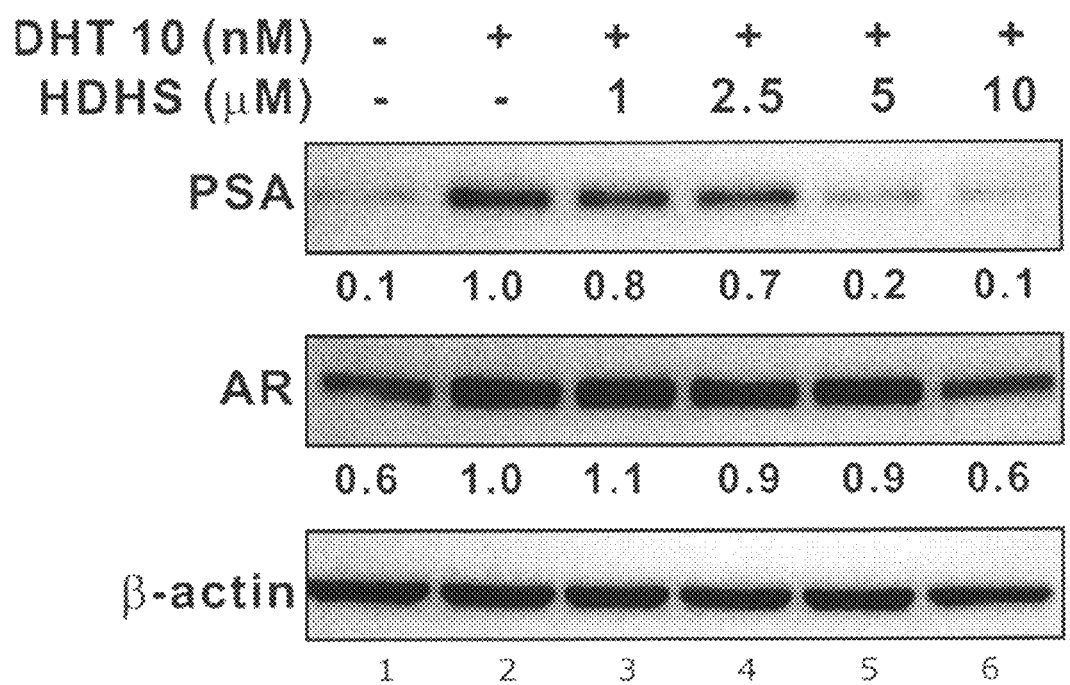
Figure 2:
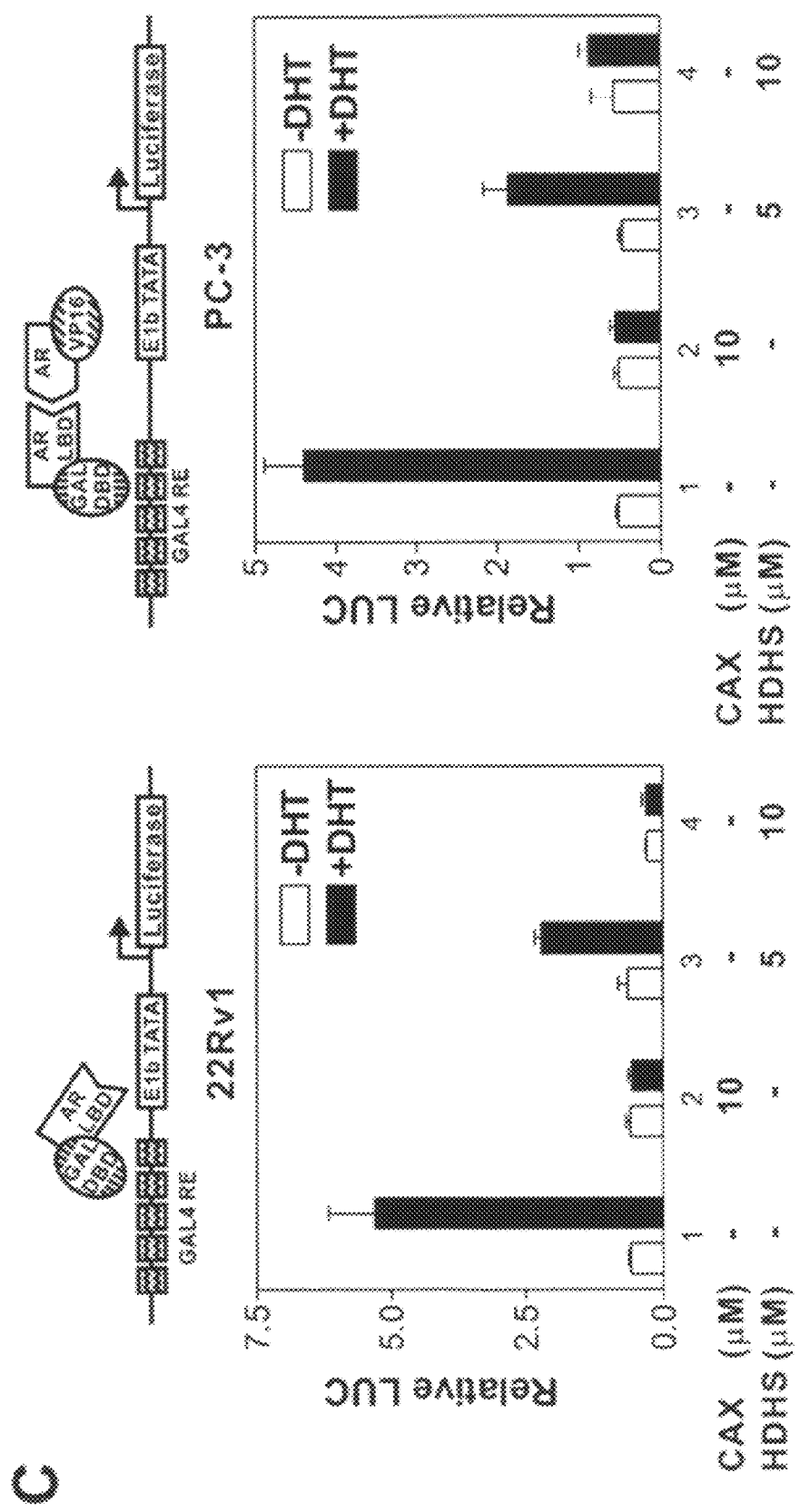
Figure 2:
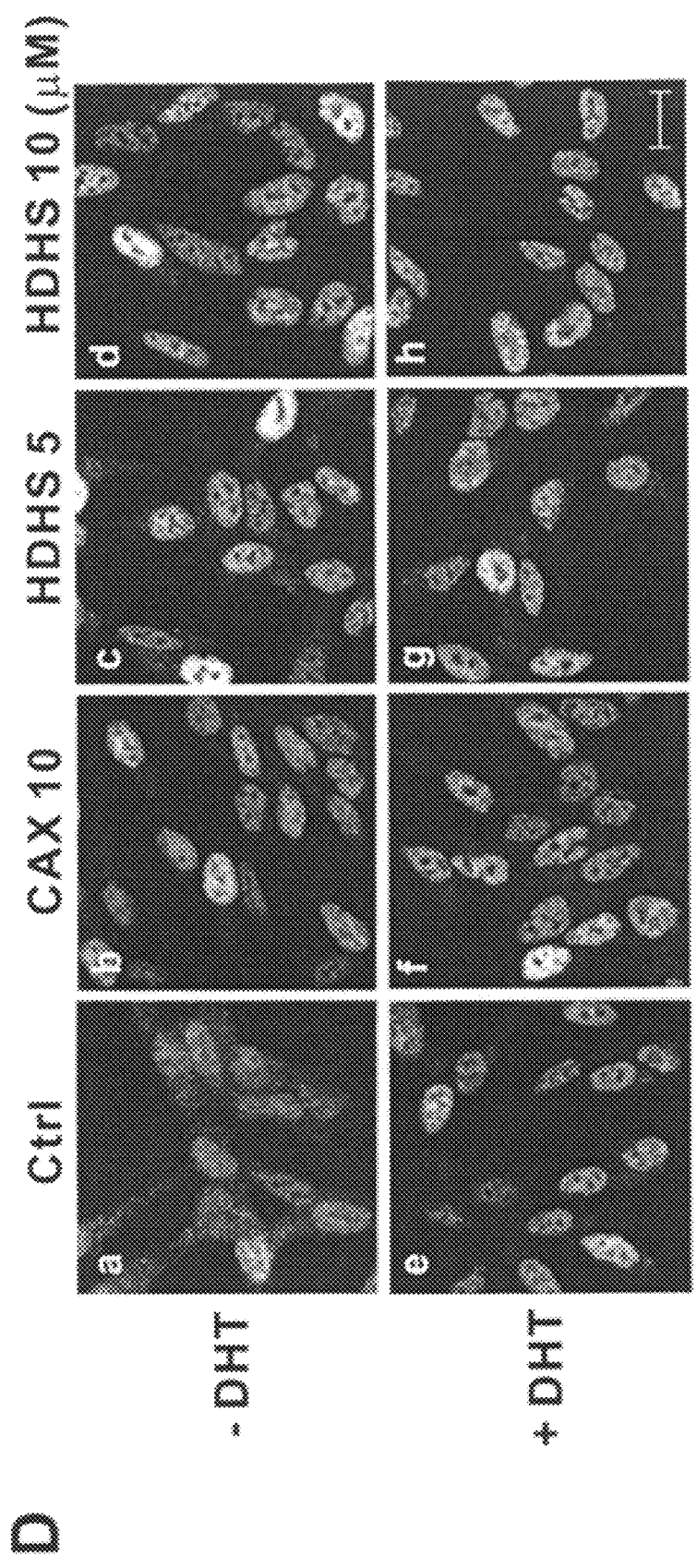

103E cells were grown and cotreated with 10 nmol/L DHT and the indicated concentrations of HDHS or CASODEX for 24 h. The PSA-luc activities of treated cells were detected and inhibition of AR activity was analyzed. Results showed that in androgen-responsive 22Rv1 cells, HDHS decreased the androgen-AR mediated activation of the PSA promoter luciferase reporter in a dose-dependent manner (FIG. 2A). In addition, HDHS was as potent as CASODEX (CAX) and achieved a complete inhibition of PSA promoter activity at concentrations greater than 10 µM (FIG. 2A). However, the slope of the HDHS dose-response curve was steeper than that of CASODEX, in which $IC_{50}$ values of HDHS and CASODEX are 4.8 and 2.5 µM, respectively (FIG. 2A).

The AR suppressing activity of HDHS was also examined in LNCaP cells, another androgen-dependent PCa cell line. LNCaP cells were treated with vehicle (Ctrl) or indicated concentrations of HDHS in the presence of 10 nM DHT for 24 h. Expression of endogenous PSA in treated cells, as a measure of cellular response to androgen, and AR activity were detected by western blot with anti-PSA and anti-AR antibodies. Protein levels (relative to actin; listed below the first two blots) were quantitatively analyzed with Chemigenius (Biolabo). The blots shown in FIG. 2B are representative of three independent experiments. As FIG. 2B shows, the intracellular expression of PSA and AR in LNCaP cells was greatly induced by DHT treatment (FIG. 2B, lane 1 vs. 2). The AR activation of PSA expression by DHT was inhibited in the presence of HDHS in a concentration-dependent manner and was completely abolished by 10 µM HDHS (FIG. 2B, lanes 3-6). The protein levels of AR in LNCaP cells were not significantly altered in cells treated with 2.5 or 5 µM HDHS, but fell to basal level in cells treated with 10 µM HDHS (FIG. 2B, lane 6 vs. 2).

Example 5

HDHS acts on Ligand-Binding Domain (LBD) of the Androgen Receptor (AR) and Induces AR Nuclear Localization The molecular mechanism whereby HDHS represses AR activity was analyzed by the following experiments. First, a one-hybrid assay was used to detect hormonal effects on nuclear receptors (Hsiao P W et al., J. Biol Chem 1999; 274:22373-9). In the one-hybrid assay, 22Rv1 cells (8×10[4] cells per well in 48-well plates) were cotransfected for 24 h with plasmids including pG5E1b-Luc (200 ng), pRL-CMV (50 ng), and pCMX-GBD-AR(DE) (175 ng) using Lipofectamine 2000 transfection reagent (Invitrogen). The transfected cells were treated with vehicle or various compounds for another 20 h. Luciferase activity was measured using the luciferase reporter gene assay system (Promega, Madison, Wis.) and normalized against Renilla luciferase values (Hsiao P W et al., J. Biol Chem 1999; 274:22373-9). Since the LBD of AR contains the AF-2, whose activation on transcription relies on binding with agonist, transcription of luciferase from the Gal4-response element can be activated upon the binding of DHT to the AR-LBD in the cells transfected with the AR-LBD fused with the Gal4 DNA-binding domain (GBD-AR-LBD) (FIG. 2C, left, lane 1). CASODEX competition with DHT for binding to the AR-LBD inhibited the DHT-induction of AR-LBD (FIG. 2C, left, lane 2 vs. 1). In this test, HDHS inhibited the AR-LBD dose-dependently just as CASODEX did (FIG. 2C, left, lanes 3 and 4 vs. 1).

Second, the AR-LBD interaction with the full-length AR can be detected by a two-hybrid interaction assay in PC-3 cells through transfection of GBD-AR-LBD and AR fused with the VP16 activation domain (AR-VP16). Specifically, PC-3 cells (1.5×10[4] cells per well in 48-well plates) were cotransfected with plasmids including pG5E1b-Luc (200 ng), pCMV-RL (50 ng), pCMX-GBD-AR(DE) (175 ng), and pCMV-VP16AR(38-918) (75 ng). The transfected cells were treated with vehicle or various compounds for another 20 h. Luciferase activity was measured using the luciferase reporter gene assay system (Promega, Madison, Wis.) and normalized against respective Renilla luciferase values. As shown by FIG. 2C, left, the two-hybrid interaction was stimulated by DHT and the DHT-induction was competitively inhibited by CASODEX and HDHS (FIG. 2C, right). These two tests indicate that HDHS affects the AR by blocking the action of DHT on the AR-LBD.

Next, it is known that DHT and CASODEX binding to the AR will induce AR nuclear translocation (Masiello D et al., J. Biol Chem 2002; 277:26321-6). A further study was conducted to examine whether HDHS treatment alone could induce AR nuclear translocation and to compare this with the effects of DHT and CASODEX. Specifically, LNCaP cells were grown in medium containing 5% charcoal-dextran stripped FBS on 12-mm coverslips for 48 h and then treated with vehicle or various compound treatments for another 1 h. Cells were fixed with 4% (v/v) paraformaldehyde on ice for 15 min, permeabilized with 0.2% (v/v) Triton X-100/PBS, and then washed with PBS three times. After blocking in 1% (v/v) fish gelatin/PBST (PBS with 0.1% Tween-20) for 1 h, samples were incubated with AR antibody (C-19, Santa Cruz) at 4° C. for 18 h, washed three times with PBST, and then probed with a fluorescence-conjugated secondary antibody (Alexa Fluor 488, Invitrogen) for 1 h at room temperature. The samples were washed again and mounted in mounting medium (Vector, Burlingame, Calif.). The cellular location of AR was visualized by confocal microscopy (LSM 510 META, Carl Zeiss GmbH, Jena, Germany) and analyzed using the manufacturer's software.

Results showed that after steroid deprivation in LNCaP cells, AR in vehicle-treated cells was distributed in the cytoplasm and nucleus (FIG. 2D, a). Treatment with DHT increased the nuclear to whole-cell ratio of AR (FIG. 2D, e). Similarly, treatment with CASODEX increased the nucleus AR ratio (FIG. 2D, b). Treatment with 5 to 10 µM of HDHS also resulted in significant AR accumulation in the nucleus (FIG. 2D, c and d). DHT cotreatment with CASODEX or HDHS also showed the same nuclear translocation of AR (FIG. 2D, f-h). As HDHS, like DHT and CASODEX, induces AR nuclear translocation, and as HDHS acts on the AR-LBD, this suggests, without intending to be bound to this mechanism, that HDHS may bind to the AR-LBD as an anti-androgen.

Example 6

HDHS Inhibits Cell Growth in Androgen-Responsive Prostate Cancer Cell Lines

Figure 3:
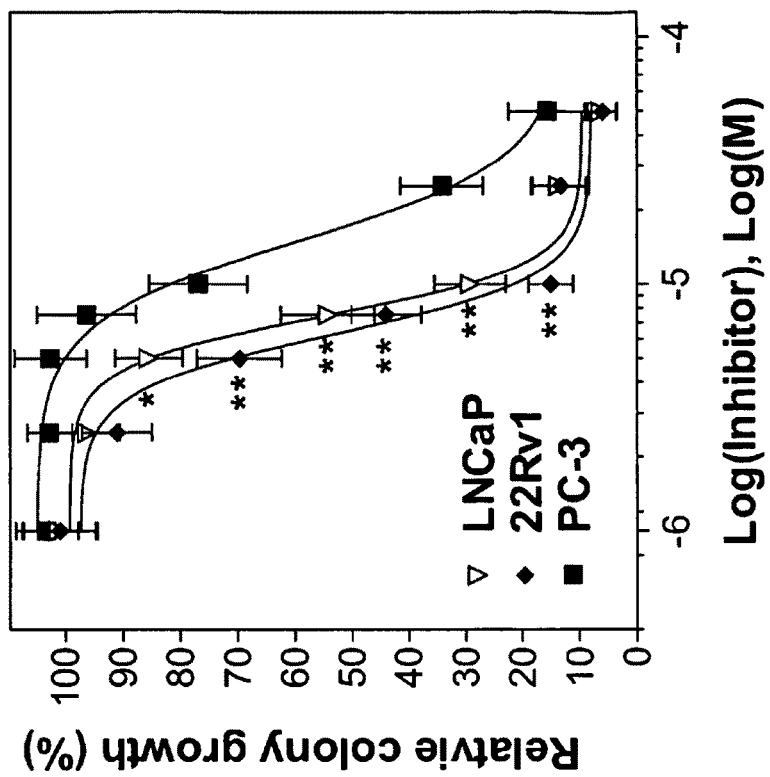
FIGS. 3A-C. HDHS affects growth of PCa cells. A, Cell viability of different cell lines treated with vehicle (Ctrl) or indicated concentrations of HDHS for 48 h. The absorbance of the control group was defined as 100%. B, Colony-forming growth of LNCaP and 22Rv1 cells (AR-dependent PCa cells) and PC-3 cells (AR-independent PCa cells) in 24-well multi-dishes with indicated treatments for 12 days. The results were presented as percentage of growth with respect to control treatment of the same cell line. C, Photographs of different PCa cell lines growing on culture plates with designated treatments for 2 days.
Figure 3:
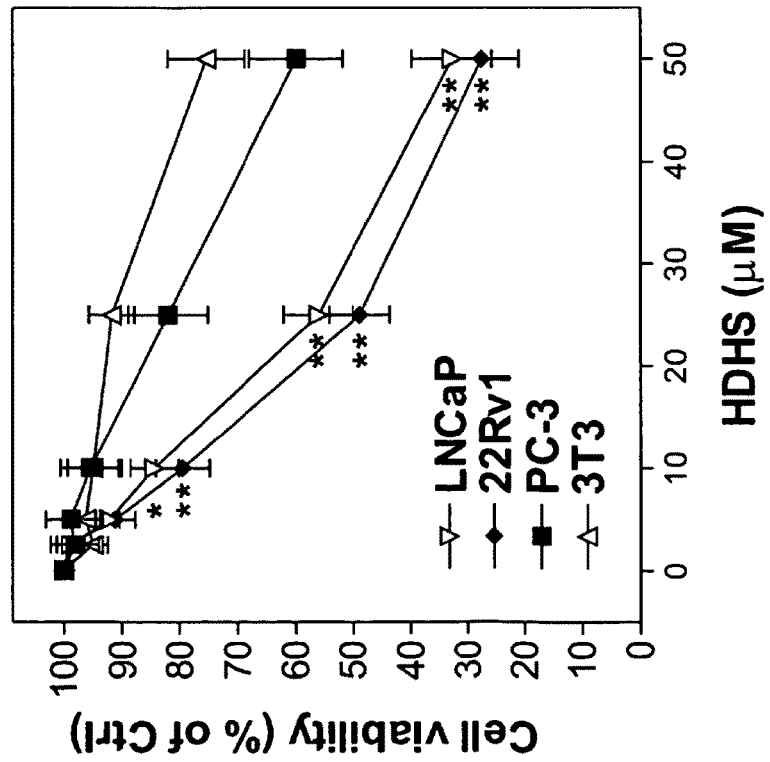
Figure 3:
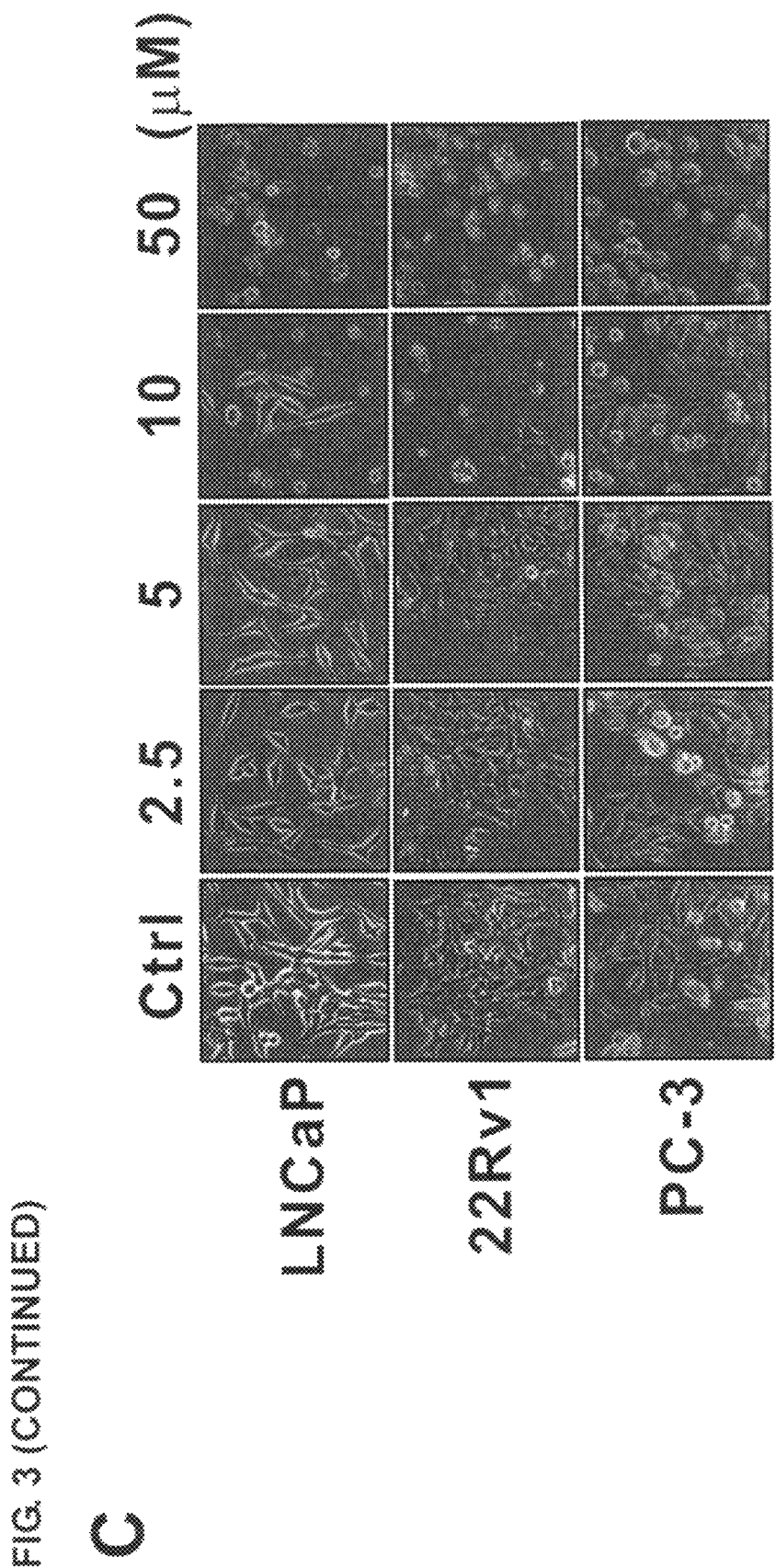

The effects of HDHS on cell viability in various PCa cell lines including androgen-dependent LNCaP, androgen-responsive 22Rv1 cells, and androgen-independent PC-3 cells were tested and compared with untransformed fibroblast NIH-3T3 cells. PCa or NIH-3T3 cells ($1 \times 10^4$ cells) were seeded into 96-well microtiter plates with 10% FBS culture medium. After 24 h, cells were incubated in 10% FBS medium containing different concentrations of HDHS or equivalent amounts of vehicle alone as control for 48 h. Cell viability was then determined by MTT assay, which quantitatively measures the metabolic activity of living cells. Results showed that HDHS concentrations above 10 µM strongly reduced cell viability in LNCaP and 22Rv1 cells but the negative effect was far less pronounced in PC-3 cells (LNCaP vs. PC-3 or 22Rv1 vs. PC-3) and NIH-3T3 cells (FIG. 3A).

The long-term effect of HDHS on the malignant growth of AR-dependent (22Rv1, and LNCaP) and AR-independent (PC-3) PCa cells was examined by colony-forming growth assay. The dose-response curves of PCa cells for relative colony growth showed that 2.5-10 µM HDHS exerted higher anti-proliferation efficacy on AR-dependent PCa cells than on AR-independent PCa cells (LNCaP vs. PC-3 or 22Rv1 vs. PC-3, FIG. 3B). The $IC_{50}$ (anti-proliferation potency) of HDHS on 22Rv1, LNCaP, and PC-3 cells was 6.3, 7.5 and 13.2 µM, respectively (FIG. 3B). The differential effect was also reflected in the morphology of treated cells. As shown in FIG. 3C, LNCaP and 22Rv1 cells treated with 10 to 50 µM HDHS for 48 h exhibited cell rounding and surface blebbing, indicating apoptosis, whereas PC-3 cells treated with up to 50 µM of HDHS exhibited only cell rounding. These results suggest that HDHS possesses potent and selective toxicity towards AR-dependent PCa cells.

Example 7

Effect of HDHS on the Cell Cycle of Different Cell Lines

The cell cycle of treated cells was examined by flow cytometry after cellular staining with propidium iodide. $5 \times 10^5$ cells were seeded into 6-well multidishes with 10% FBS culture medium for 48 h. Cells were treated with HDHS, CASODEX or vehicle for 48 h. Cells were trypsinized thereafter, washed twice with cold PBS, and centrifuged. The pellet was suspended in cold PBS and 1 mL of 70% ethanol at 4° C. overnight, washed twice with cold PBS, and digested with RNase (100 µg/mL final concentration) and stained with propidium iodide (10 µg/mL final concentration) for 30 min and analyzed by flow cytometry (EPICS XL-MCL, Beckman Coulter, Inc., Fullerton, Calif.).

The effects of HDHS on the cell cycle distribution of PCa cells are shown in Table 2. After HDHS treatment for 48 h, there was a significant increase in the sub-G1 cell population along with decreases in the G0-G1 and S populations in both LNCaP and 22Rv1 cells, whereas in PC-3 cells there was an increase in the G0-G1 population and a decrease in the G2-M population without any significant change in sub-G1 populations in comparison with vehicle-treated controls. The alteration of cell cycle profiles in AR-dependent PCa cells upon HDHS treatment was highly dose-dependent. In LNCaP and 22Rv1 cells, the G0-G1 populations modestly increased with 5 µM HDHS, and drastically decreased with 10 µM HDHS; meanwhile, the sub-G1 populations surged. HDHS treatment for 24 h resulted in similar effects as those seen at 48 h except for lower degrees of alterations in all tested cell lines (data not shown). In contrast, treatment with 1 to 10 µM CASODEX showed no appreciable change in the cell cycle distribution in any of the three PCa cell lines.

TABLE 2

Effect of CAX and HDHS on cell cycle distribution in AR-dependent and AR-independent PCa cells

| Treatments | $G_0$-$G_1$ phase | $G_2$-M phase | S phase | Sub-$G_1$ phase |
|---|---|---|---|---|
| LNCaP cells | | | | |
| Ctrl | 61.7 ± 1.7 | 22.0 ± 1.9 | 11.2 ± 1.2 | 0.9 ± 0.5 |
| CAX 1 µM | 62.1 ± 3.5* | 21.8 ± 2.0* | 10.1 ± 1.7* | 1.0 ± 0.5* |
| CAX 10 µM | 61.3 ± 3.4* | 22.3 ± 1.7* | 10.4 ± 1.5* | 1.3 ± 0.8* |
| HDHS 2.5 µM | 62.6 ± 2.8* | 21.1 ± 2.4* | 11.5 ± 2.1* | 0.8 ± 0.4* |
| HDHS 5 µM | 66.9 ± 2.0† | 18.7 ± 3.5* | 8.1 ± 1.8† | 3.9 ± 0.7† |
| HDHS 10 µM | 45.1 ± 3.1‡ | 20.2 ± 2.1* | 6.8 ± 2.4* | 24.3 ± 3.1‡ |
| 22Rv1 cells | | | | |
| Ctrl | 52.7 ± 2.7 | 25.8 ± 2.1 | 13.4 ± 1.5 | 1.4 ± 0.6 |
| CAX 1 µM | 53.5 ± 2.6* | 25.0 ± 1.6* | 13.5 ± 2.3* | 1.5 ± 1.1* |
| CAX 10 µM | 53.0 ± 3.2* | 25.4 ± 1.0* | 12.2 ± 1.8* | 2.3 ± 1.8* |
| HDHS 2.5 µM | 54.5 ± 2.5* | 24.8 ± 2.4* | 11.2 ± 1.9* | 2.2 ± 0.8* |

TABLE 2-continued

Effect of CAX and HDHS on cell cycle distribution
in AR-dependent and AR-independent PCa cells

| Treatments | $G_0$-$G_1$ phase | $G_2$-M phase | S phase | Sub-$G_1$ phase |
|---|---|---|---|---|
| HDHS 5 μM | 57.9 ± 1.9† | 23.7 ± 2.7* | 8.0 ± 1.4‡ | 3.8 ± 0.9† |
| HDHS 10 μM | 48.4 ± 2.9‡ | 24.5 ± 2.0* | 5.7 ± 2.2‡ | 14.4 ± 3.7‡ |
| PC-3 cells | | | | |
| Ctrl | 50.0 ± 2.2 | 26.1 ± 2.1 | 19.8 ± 1.6 | 2.0 ± 0.8 |
| CAX 1 μM | 51.1 ± 3.6* | 24.4 ± 2.5* | 18.5 ± 2.1* | 2.3 ± 1.5* |
| CAX 10 μM | 51.0 ± 2.1* | 25.2 ± 2.1* | 19.0 ± 1.3* | 1.8 ± 1.4* |
| HDHS 2.5 μM | 52.7 ± 2.0* | 24.9 ± 2.7* | 19.2 ± 1.0* | 2.3 ± 0.7* |
| HDHS 5 μM | 55.9 ± 2.9† | 19.5 ± 2.9† | 18.8 ± 1.1* | 2.8 ± 0.9* |
| HDHS 10 μM | 58.2 ± 2.8‡ | 19.2 ± 3.2† | 18.0 ± 1.9* | 2.1 ± 0.6* |

NOTE:
The cells were treated with vehicle alone or indicated dose of drugs for 48 hours, stained with propidium iodide, and analyzed by flow cytometry. Percentages of cell population in sub-$G_1$, $G_0$-$G_1$, S, and $G_2$-M phases were calculated using EXPO32 ADC analysis. Each value represents the mean ± SD from two independent experiments of four replicates. Each indicated treatment versus vehicle control was statistically compared by paired t-test.
*P = not significant.
†P ≦ 0.05.
‡P ≦ 0.01.

Example 8

HDHS Induces Apoptosis in AR-Expression Prostate Cancer Cells

In light of the increase of sub-G1 populations by HDHS, apoptosis in treated cells was further analyzed via measurement of nucleosome release in PCa cells. Apoptosis was significantly induced in LNCaP and 22Rv1 cells treated with 5-10 μM HDHS for 24 h, but not in PC-3 cells (FIG. 4A). 22Rv1 cells with AR expression are ablation-resistant but respond to androgen stimulation; HDHS led to their apoptosis. These data also suggest that a similar mechanism may mediate the effects of HDHS on cell cycle progression in both LNCaP and 22Rv1 cells. On the other hand, treatment of 22Rv1 cells with CASODEX up to 10 μM for 24 h, failed to induce apoptosis.

Figure 4:
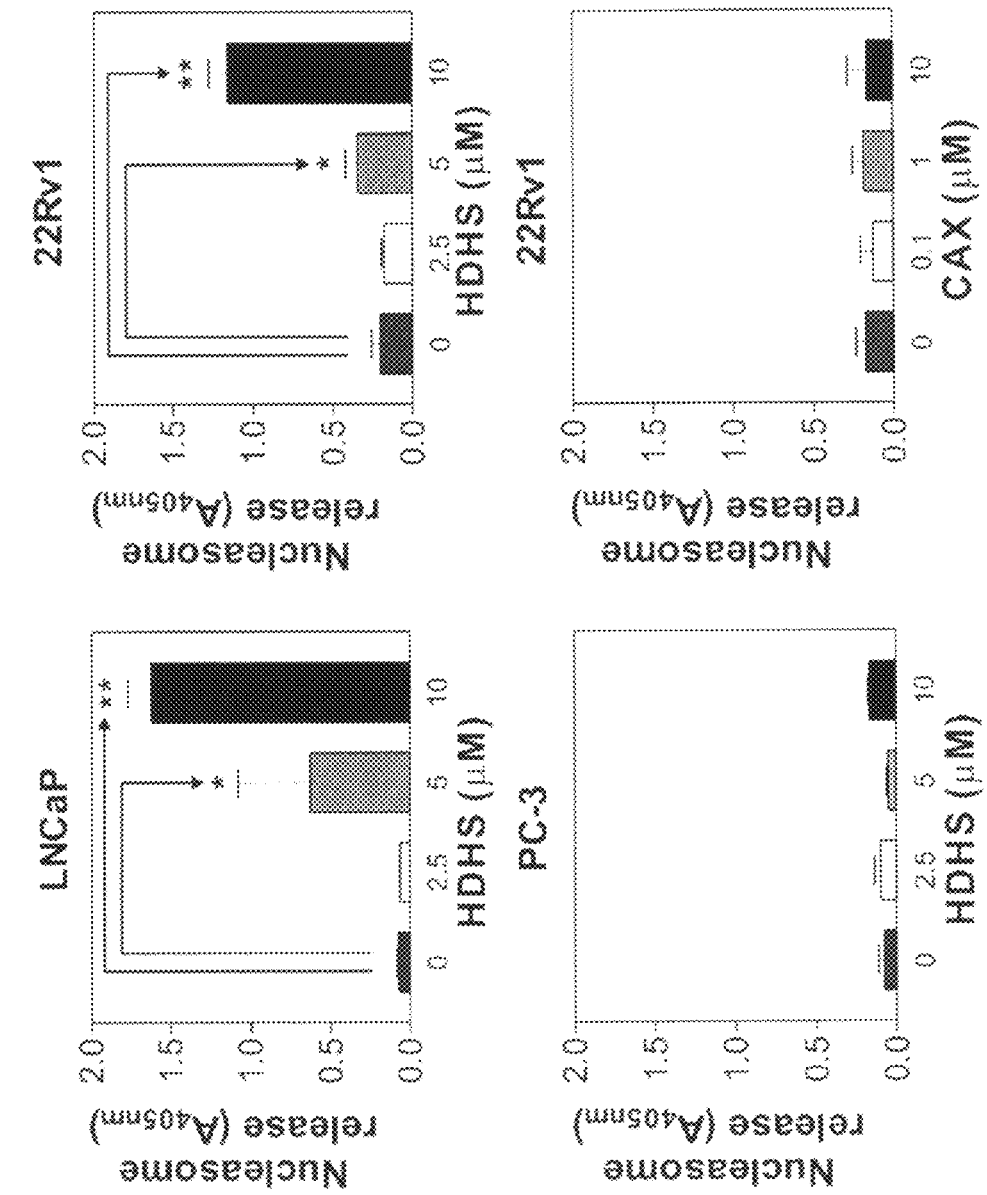
FIGS. 4A-B. HDHS induces apoptosis in AR-dependent PCa cells. A, Apoptosis of cytoplasmic DNA fragmentation in different cell lines treated with vehicle or indicated concentrations of HDHS for 24 h. Difference between the indicated pair of treatments was tested for statistic significance as marked. *, $P \leq 0.05$; **, $P \leq 0.01$. B, Activation of caspases and PARP in HDHS-induced apoptosis of LNCaP cells.

During apoptosis, various caspases are activated which are involved in the cleavage and activation of a range of cellular substrates, including activation of the DNA repair enzyme PARP (Herceg Z et al., Mol Cell Biol 1999;10:5124-33; Okada H et al., Nat Rev Cancer 2004; 4:592-603). In the presence of 10 μM HDHS, PARP cleavage was observed, and at the same time caspase-3 and -7 were activated by proteolytic cleavage (FIG. 4B, lane 5). These results confirmed the flow cytometry observation that HDHS stimulates apoptosis in LNCaP cells (Table 1) and the observed nucleosome release (FIG. 4A). In contrast, activation of caspase-3 and -7 or cleavage of PARP were not detected in PC-3 cells treated with 10 μM HDHS for 24 h (FIG. 4B, lane 10). Tumor suppressor p53 is a control for the G1 checkpoint and cell apoptosis, and LNCaP cells express wild-type p53 (van Bokhoven A et al., Prostate 2003; 57:205-25). LNCaP cells treated with 10 μM HDHS for 24 h had a 3-fold increase in p53; concurrently, levels of the anti-apoptotic regulator Bcl-xL decreased by ~50% (FIG. 4B, lane 5).

Example 9

Figure 5:
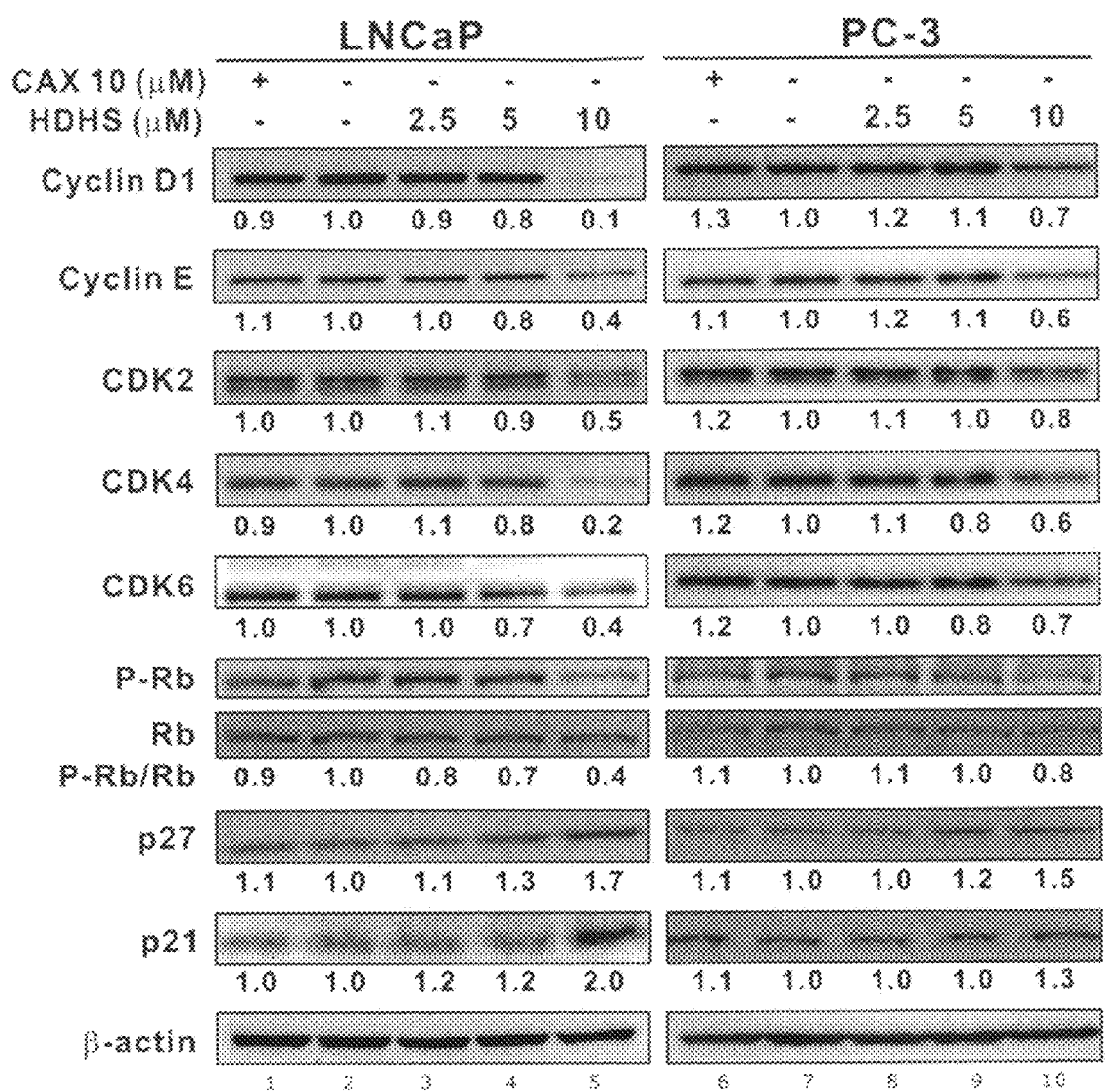
FIG. 5. Western blot analysis indicates that HDHS blocks cell cycle progression at G1 phase and the protein expression of G1-associated cyclins and CDKs in LNCaP and PC-3 cells.

HDHS Decreases Expression of G1-Associated Cyclins and CDKS in LNCAP and PC-3 Cells The molecular mechanisms for HDHS-induced G0-G1 cell cycle arrest were further assessed by the expression of the cyclins and CDKs that operate in the G1 phase in PCa cells (Malumbres M et al., Nat Rev Cancer 2001; 1:222-31; Massague J. Nature 2004; 432:298-306). HDHS treatment of LNCaP cells for 24 h resulted in a concentration-dependent decrease in cyclins D1 and E (FIG. 5, lanes 3-5). Moreover, HDHS also decreased the protein levels of CDK4, CDK6, and CDK2 (FIG. 5, lanes 3-5). Protein expression of CDK inhibitors operative at the G1 checkpoint, p21 and p27, also increased in the presence of 10 μM HDHS (FIG. 5, lane 5). The HDHS-mediated down-regulation of CDKs and cyclins together suggest that CDK kinase activity and the consequent phosphorylation of Rb may decrease. Indeed, HDHS treatment markedly decreased the phosphorylation of Rb in LNCaP cells (FIG. 5, lanes 3-5). All the above phenomena were also observed in PC-3 cells treated with HDHS, only at a lower magnitude than in LNCaP cells (FIG. 5 lane 10 vs. 5). As a comparison, CASODEX treatment in LNCaP and PC-3 cells (FIG. 5, lanes 1 and 6) failed to lead to any significant change in cell cycle (Table 1). Taken together, these results indicate that HDHS induces apoptosis in AR-dependent PCa cells by arresting cell cycle at the G1-checkpoint and activating apoptotic signaling pathways, whereas only cell cycle arrest was observed in AR-independent PCa cells upon HDHS treatment.

Example 10

Oral Intake of HDHS Suppresses Growth of PCA 22Rv1 Xenograft in Nude Mice

22Rv1 cells were derived from a castration-relapsed tumor of human PCa origin that represents a clinical limitation for hormonal therapy (Nagabhushan M, et al., Cancer Res 1996; 56:3042-6; Sramkoski R M, et al., In Vitro Cell Dev Biol Anim 1999; 35:403-9). The potential of HDHS to inhibit growth of PCa in vivo was tested in athymic nude mice with 22Rv1 tumors. Athymic (nu/nu) nude mice (6-7 weeks of age) were obtained from the National Laboratory Animal Center and housed in the Laboratory Animal Center of the National Defense Medical Center, Taipei, Taiwan under conditions of constant photoperiod (12 h light/12 h dark) and fed with Laboratory Autoclavable Rodent Diet 5010 (LabDiet, Richmond, Ind.). All animal work was done in accordance with the protocol approved by the Institutional Animal Care and Use Committee, Academia Sinica. Aliquots of $1 \times 10^6$ 22Rv1 cells were suspended in 1:1 PBS mixed with Matrigel (BD Biosciences, San Jose, Calif.) and were subcutaneously inoculated into the right flank of each mouse. Once the tumor grew to palpable size one week after 22Rv1 cells were implanted, mice were stochastically assigned to three groups (n=7) that received vehicle control or HDHS at different dosages (0.5 and 2.5 mg/kg/day), by gavage in 0.2 mL of PBS containing 10% DMSO. Tumors were measured twice per week using calipers and their volumes calculated using a standard formula, as follows: width2×length×0.5. Body weight was measured weekly. Mice received 24 doses, and 24 h after the last dose they were sacrificed to harvest plasma and tumors. A portion of each tumor was snap-frozen in liquid nitrogen and stored at −80° C. until needed for western blot analysis of relevant biomarkers, and the remainder was fixed in 10% formalin overnight.

Figure 6:
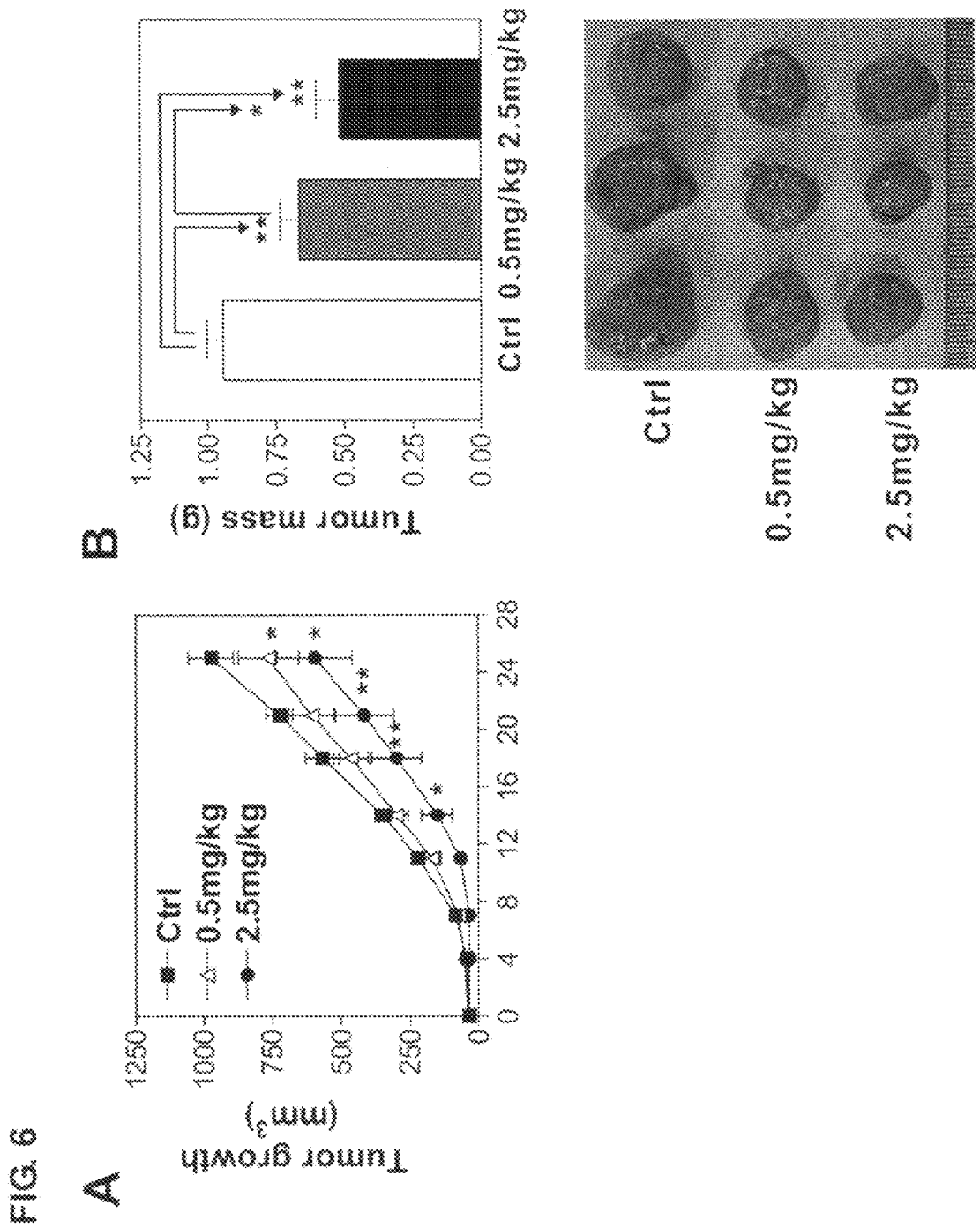
FIGS. 6A-D. HDHS suppresses tumor growth of CWR22Rv1 xenograft in nude mice via inducing apoptosis and diminishing proliferation and AR expression. A, Mean tumor volume for each treatment group presented as growth curves. Points, mean; bars, ±SE (n=7). B, endpoint tumor mass. Upper, tumor mass of each treatment group was statistically analyzed for significant difference as marked. *, $P \leq 0.05$; **, $P \leq 0.01$. Lower, photograph of dissected tumors representing all tested groups. C, Mean body weight for each treatment group plotted as a function of day of treatment. D, Tumors excised at the end of the xenograft study and processed for immunohistochemical staining for proliferation with Ki-67 (a-c), apoptosis by TUNEL assay (d-f), and AR expression (g-i). A representative picture of each treatment group is shown. Right, Ki-67-postive and TUNEL-positive density (%) were calculated by [number of positive (reddish brown) cells×100/total number of cells counted]. Each treatment group was statistically analyzed and significant differences are marked. *, $P \leq 0.05$; **, $P \leq 0.01$.
Figure 6:
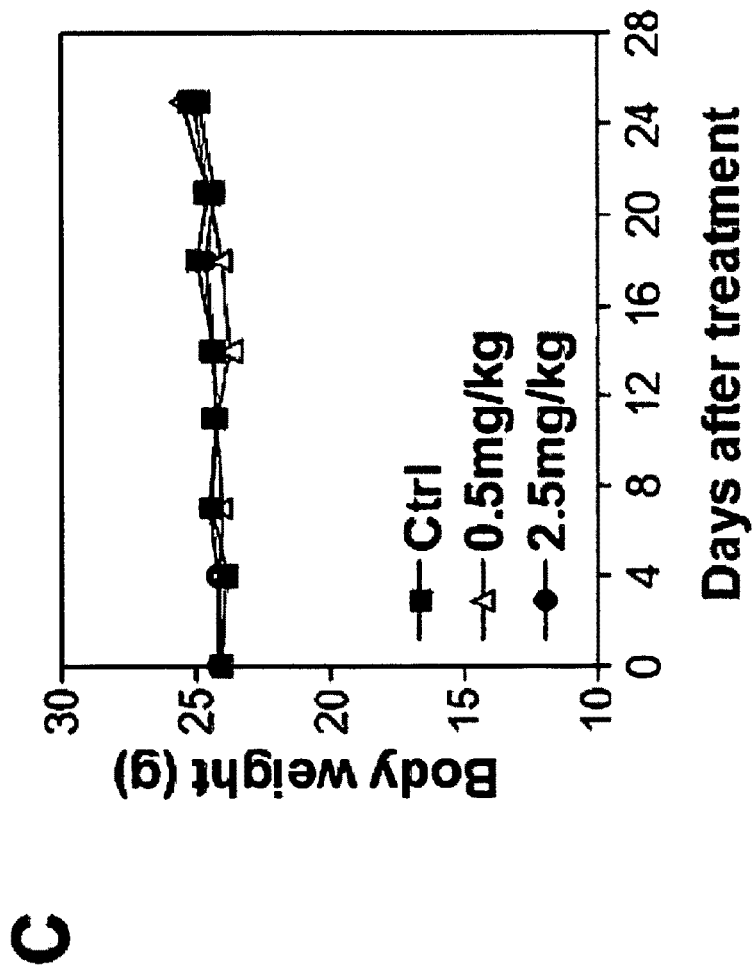
Figure 6:
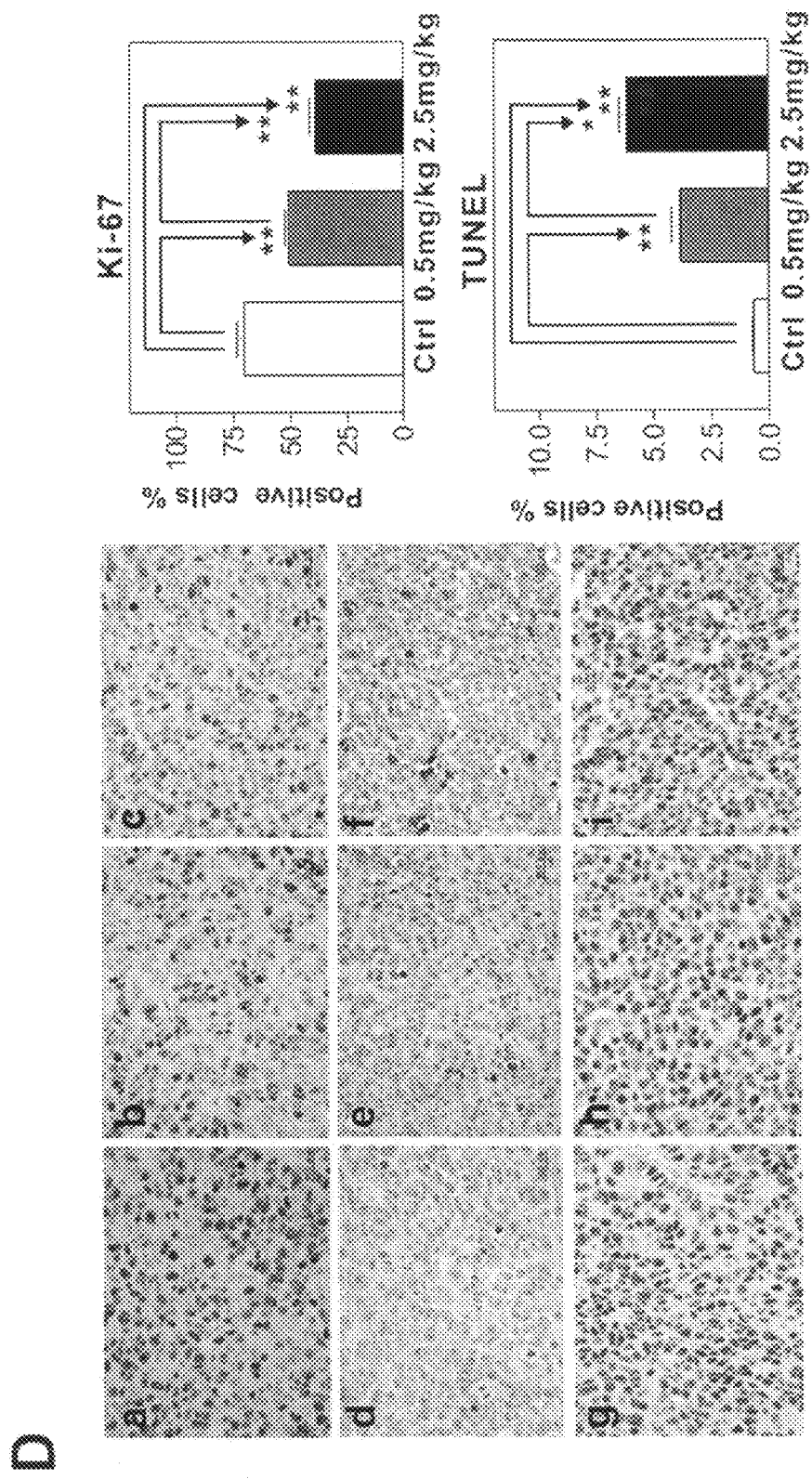
Figure 7A:
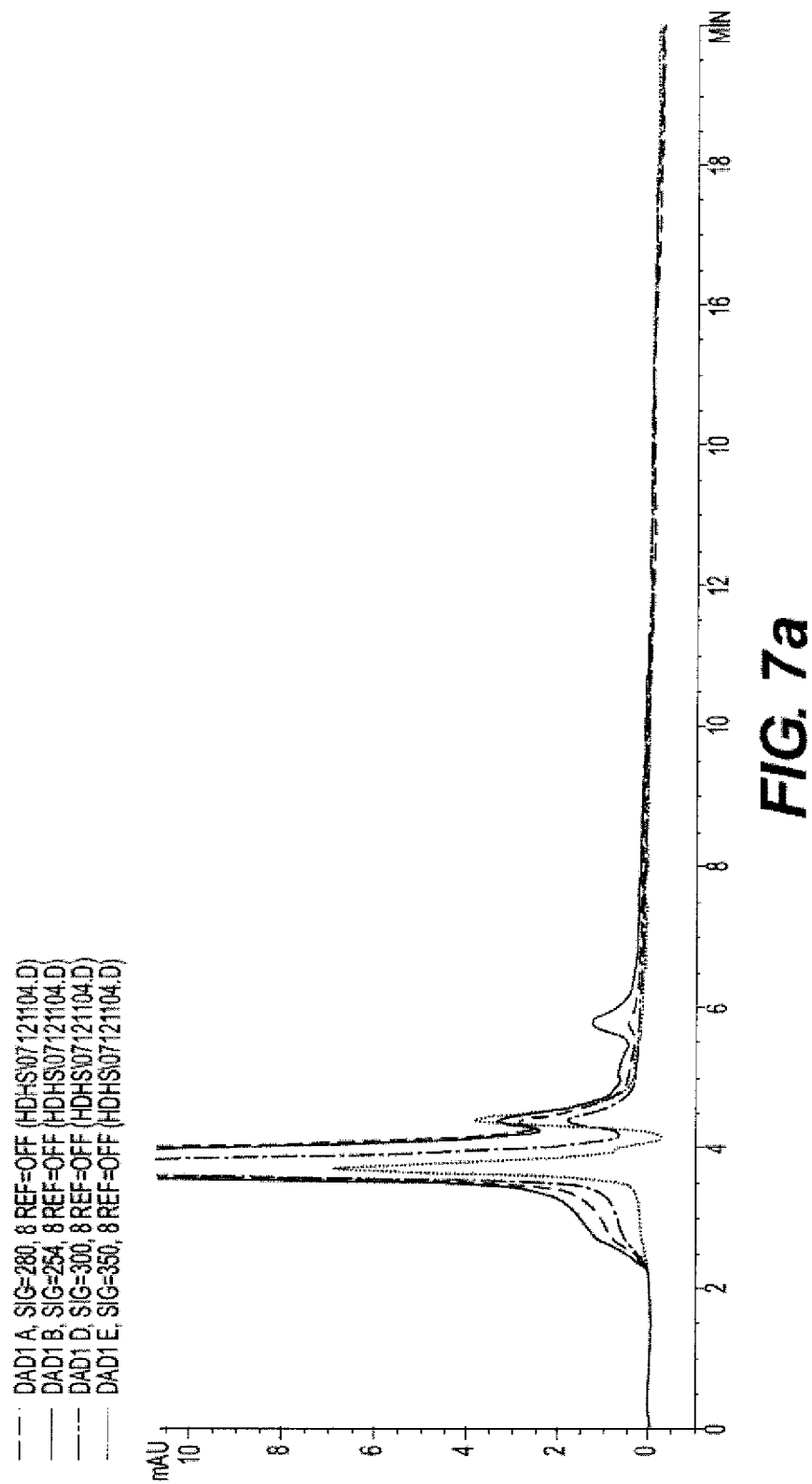
FIGS. 7A-E. Pharmacologically attainable HDHS levels in the plasma and implanted 22Rv1 tumor of treated nude mice. A, HPLC chromatograms of HDHS extracted from plasma samples. Chromatograms from blank plasma (a), vehicle control group (b), 0.5 mg/kg group (c), 2.5 mg/kg group (d), and plasma samples of (d) spiked with 10 uM HDHS (e).
Figure 7B:
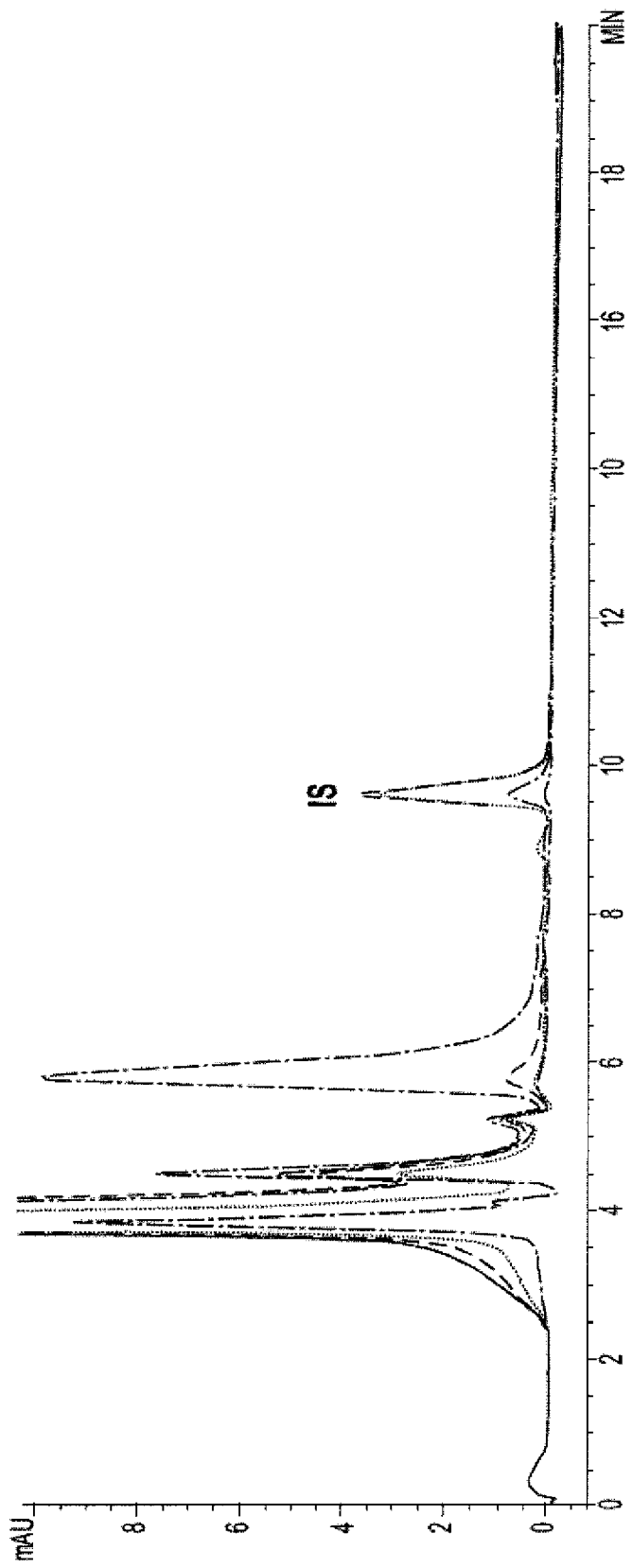
Figure 7C:
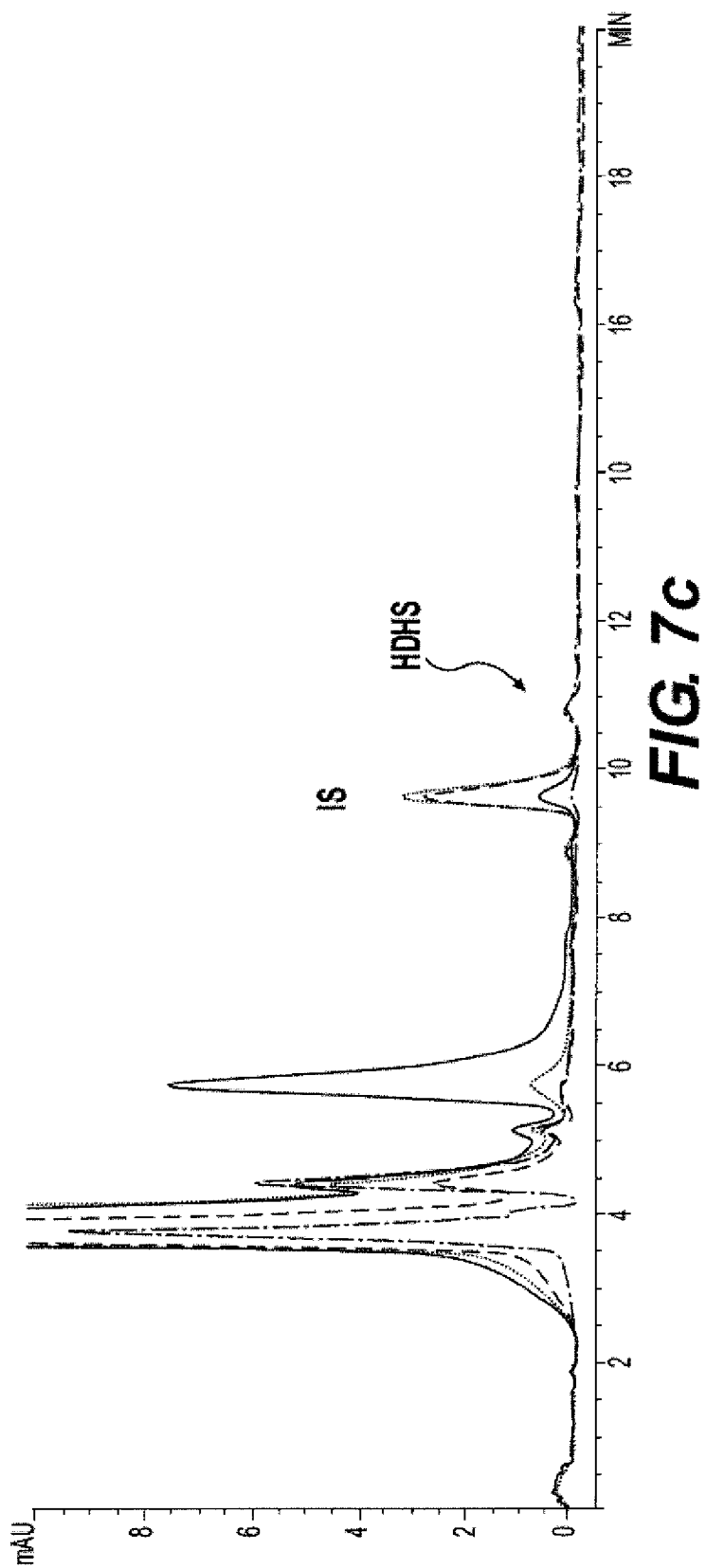
Figure 7D:
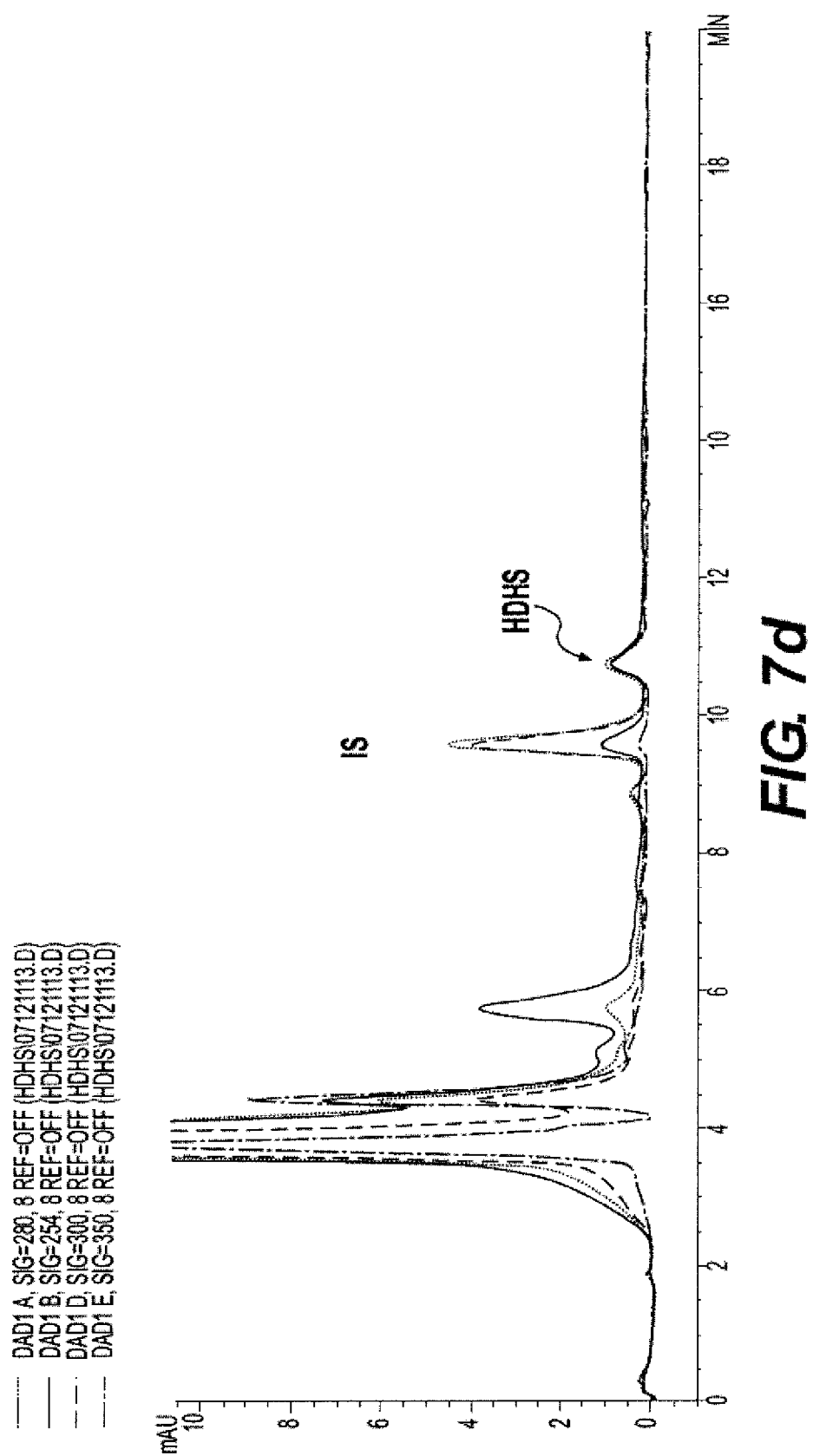
Figure 7E:
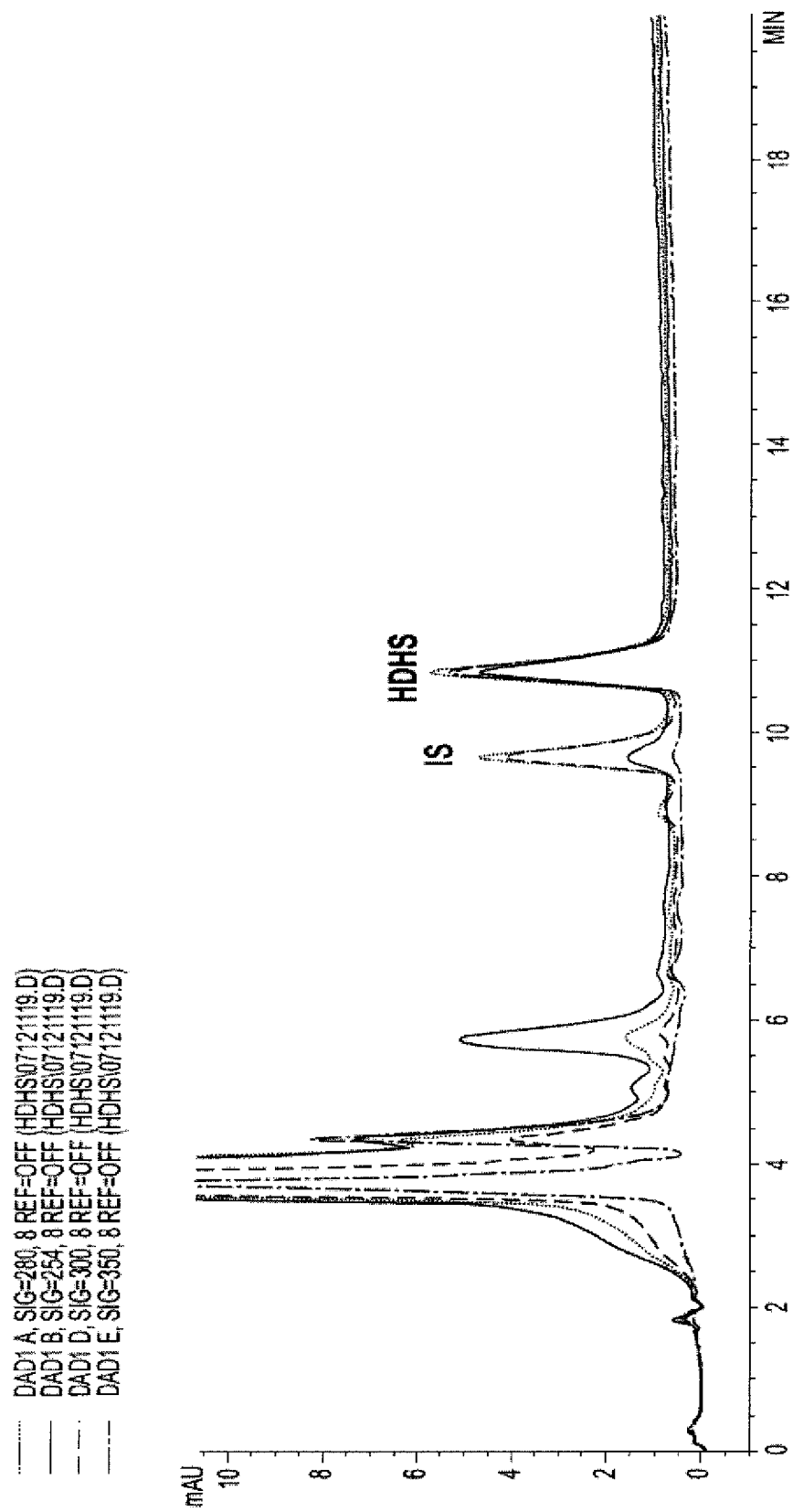

Results revealed that oral intake of HDHS significantly retarded tumor growth (FIGS. 6A and 6B). End-point tumor mass showed the dose-dependent suppression effects of HDHS (0.5 vs. 2.5 mg/kg, P≦0.05, FIG. 6B). During the 24-day HDHS regimen, mice did not exhibit any symptoms of toxicity such as loss of appetite, decreased locomotion, or any other apparent signs of illness. As shown in FIG. 6C, body weight of tested mice was not influenced by HDHS at up to 2.5 mg/kg per day.

Immunohistochemistry was conducted to examine the in vivo effects of HDHS on proliferation and apoptosis in tumor xenografts. The paraffin-embedded tumor sections (4 μm thickness) were heat immobilized, deparaffinized using xylene and rehydrated in a graded series of ethanol with a final wash in distilled water. Antigen retrieval was done in TARGET RETRIEVAL SOLUTION (DakoCytomation, Glostrup, Denmark) in a DECLOAKING CHAMBER (Biocare Medical, Concord, Calif.) followed by quenching of endogenous peroxidase activity. Sections were then incubated with specific primary antibodies, including mouse monoclonal anti-Ki-67 (DakoCytomation) and rabbit polyclonal anti-AR (Santa Cruz) at 4° C. overnight in a humidity chamber. An ENVISION system (DakoCytomation) was used to detect the reaction products. In situ detection of apoptotic cells was carried out using terminal deoxynucleotidyl transferase-mediated nick-end labeling (TUNEL assay) reaction mixture according to the manufacturer's protocol (Chemicon).

Staining for proliferative tumor cells with human-specific Ki-67 antibody further revealed that oral intake of 0.5 and 2.5 mg/kg/day HDHS for 24 days decreased the number of cells positively stained for Ki-67 (FIG. 6D, a-c) and resulted in an increase of apoptotic tumor cells, positively stained by the TUNEL method (FIG. 6D, d-f). The anti-proliferation and apoptosis induction effects of HDHS were statistically significant and the results were dose-dependent (FIG. 6D, right). Moreover, we stained the AR expression in tumor cells, which also indicated activity of the androgen-AR axis. A prevalent decrease of AR expression was found in HDHS-treated tumors, while they remained positively stained for AR (FIG. 6D, g-i). This result agreed with the in vitro effect of HDHS (FIG. 2B) and suggested a debilitating activity of AR in vivo.

Example 11

Figure 8:
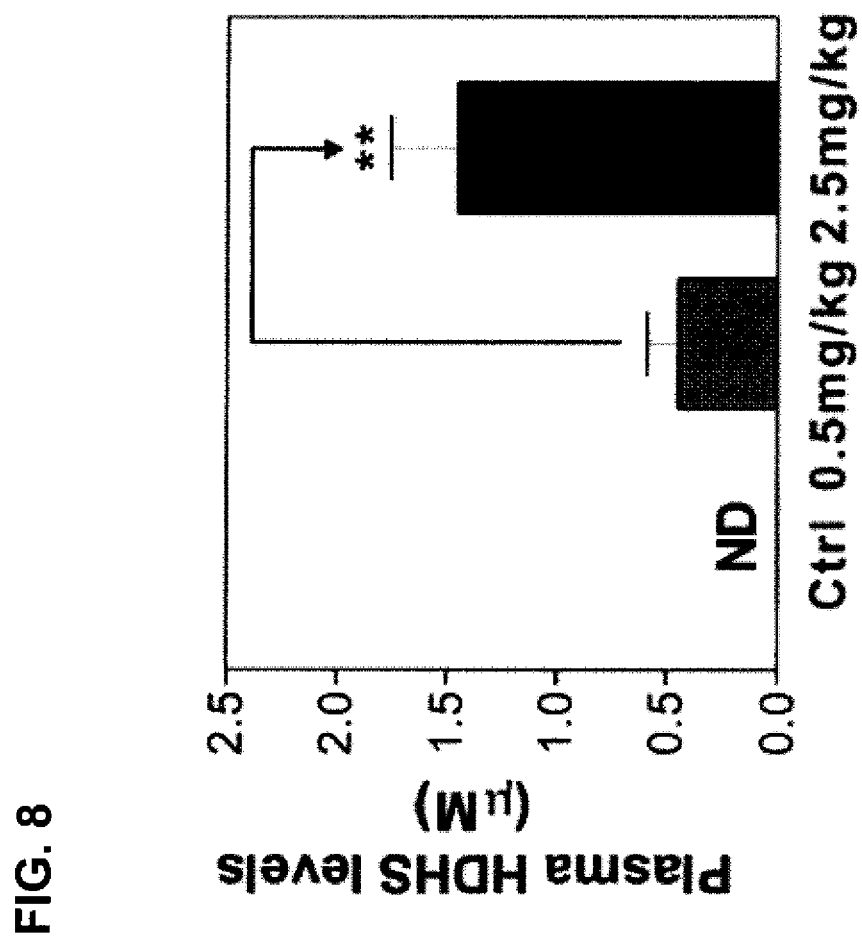
FIG. 8. Average HDHS levels in mouse plasma. Difference between oral intake of 0.5 mg/kg and 2.5 mg/kg groups was analyzed and significance was as marked. *, $P<0.05$; **, $P<0.01$.
Figure 9A:
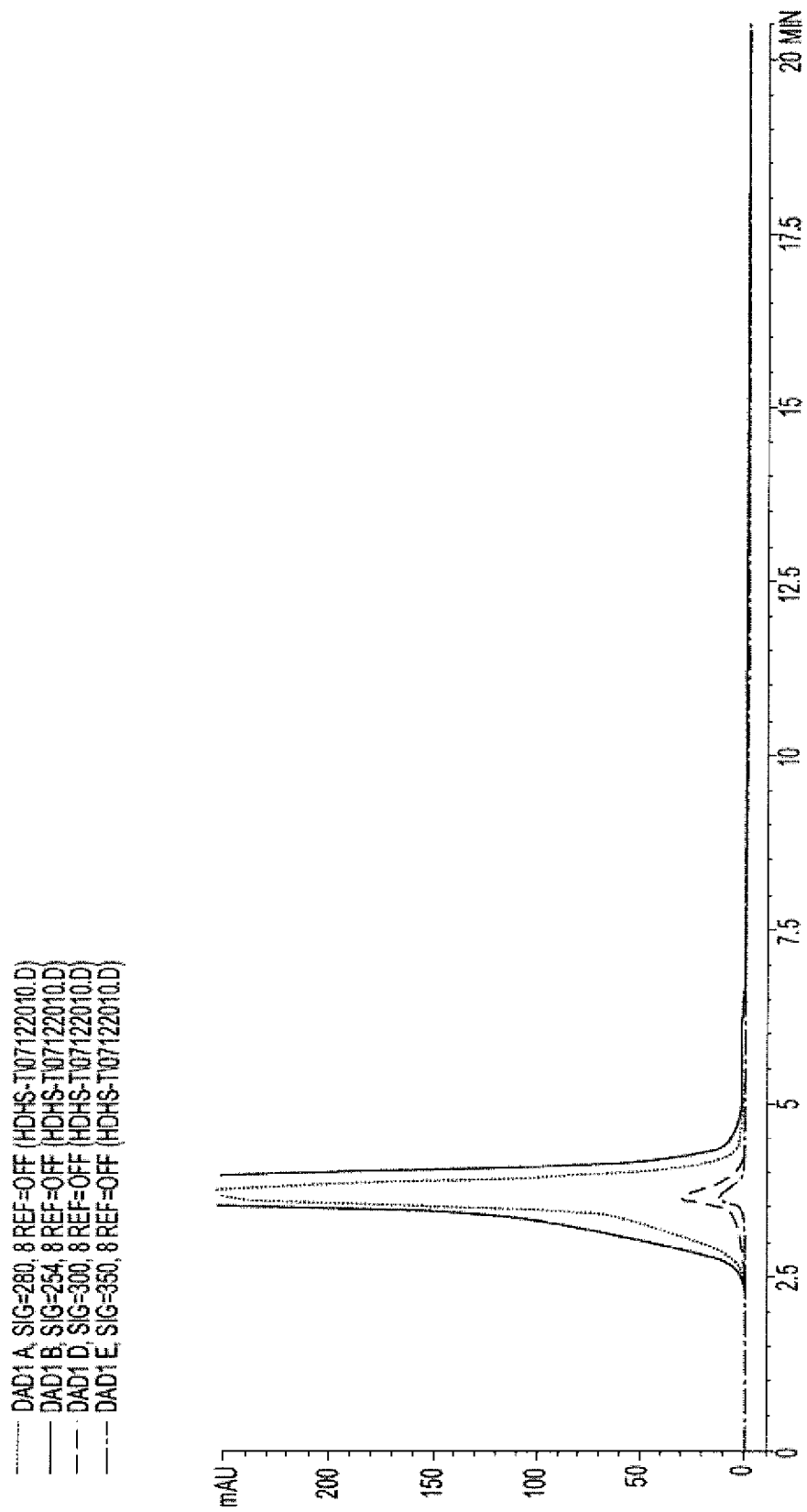
Figure 9B:
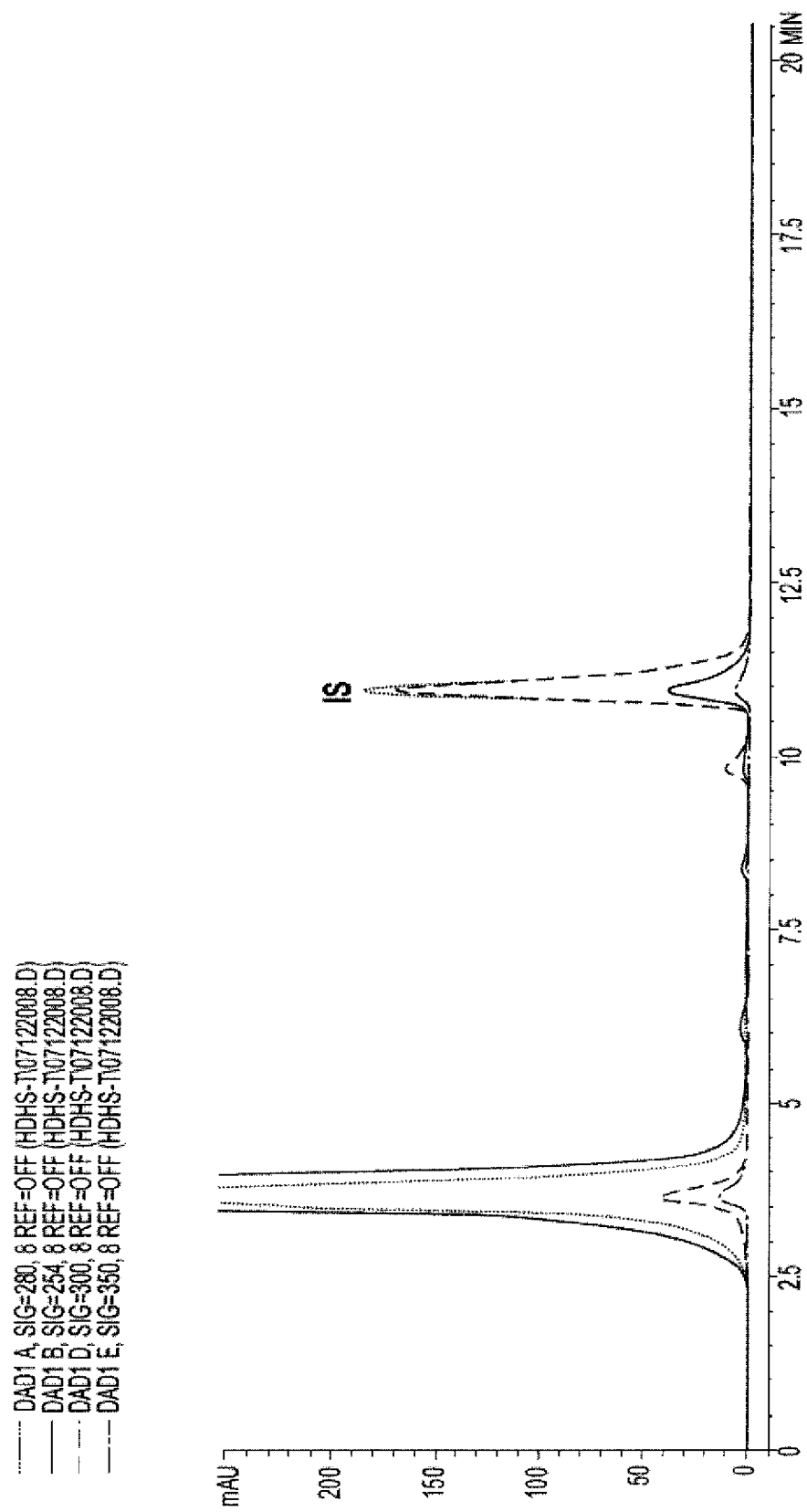
Figure 9C:
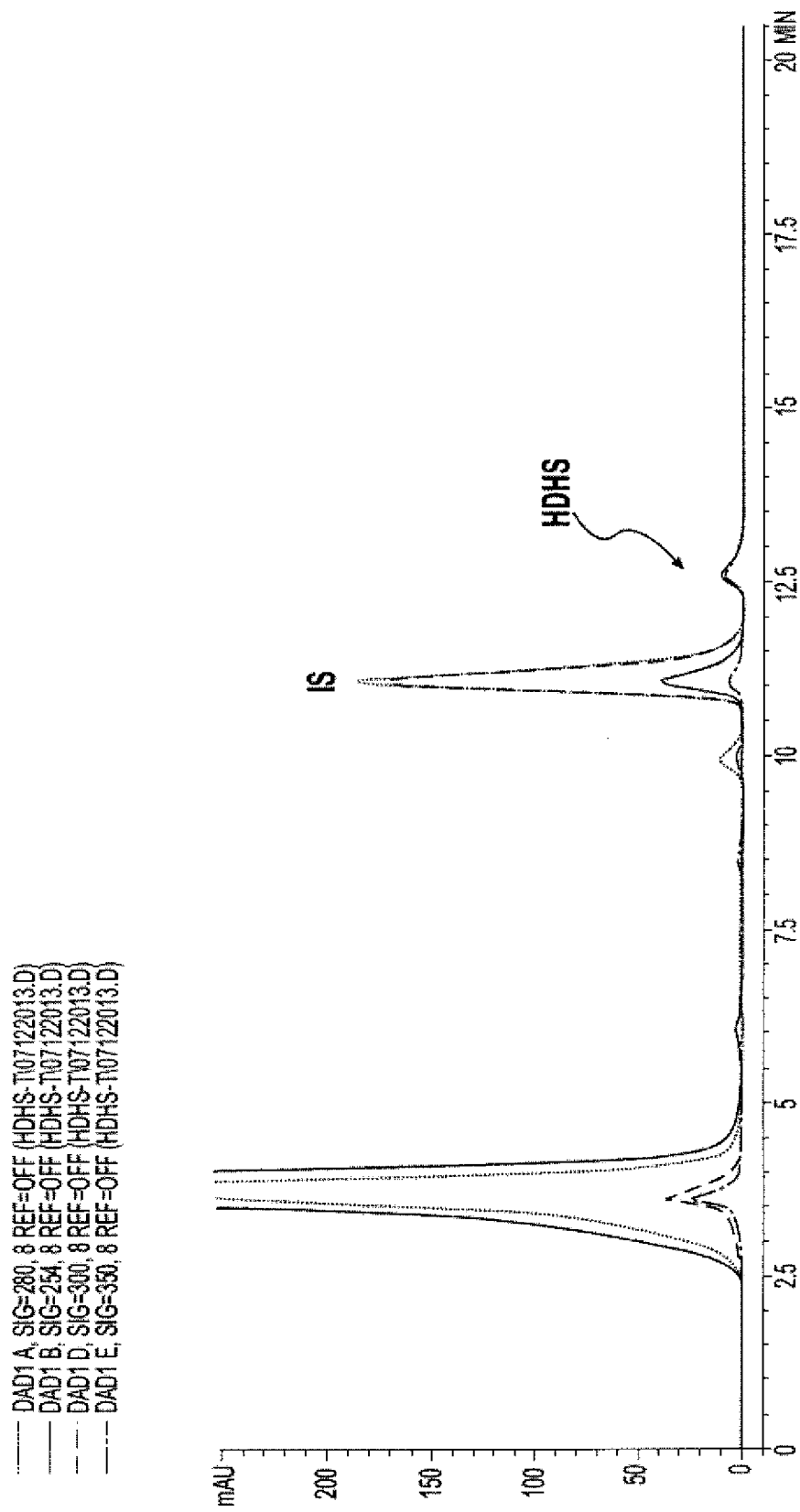
Figure 9E:
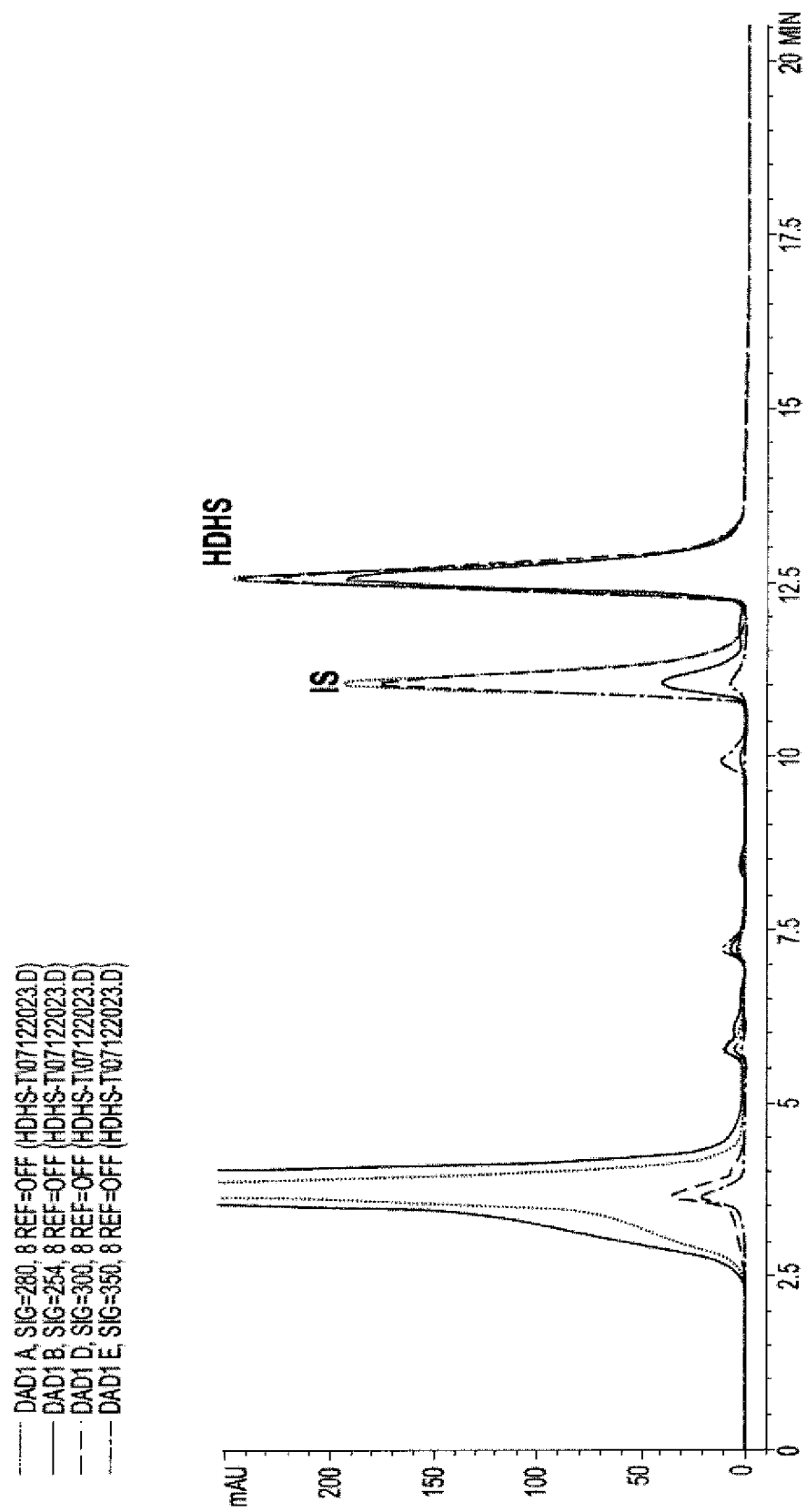
Figure 10:
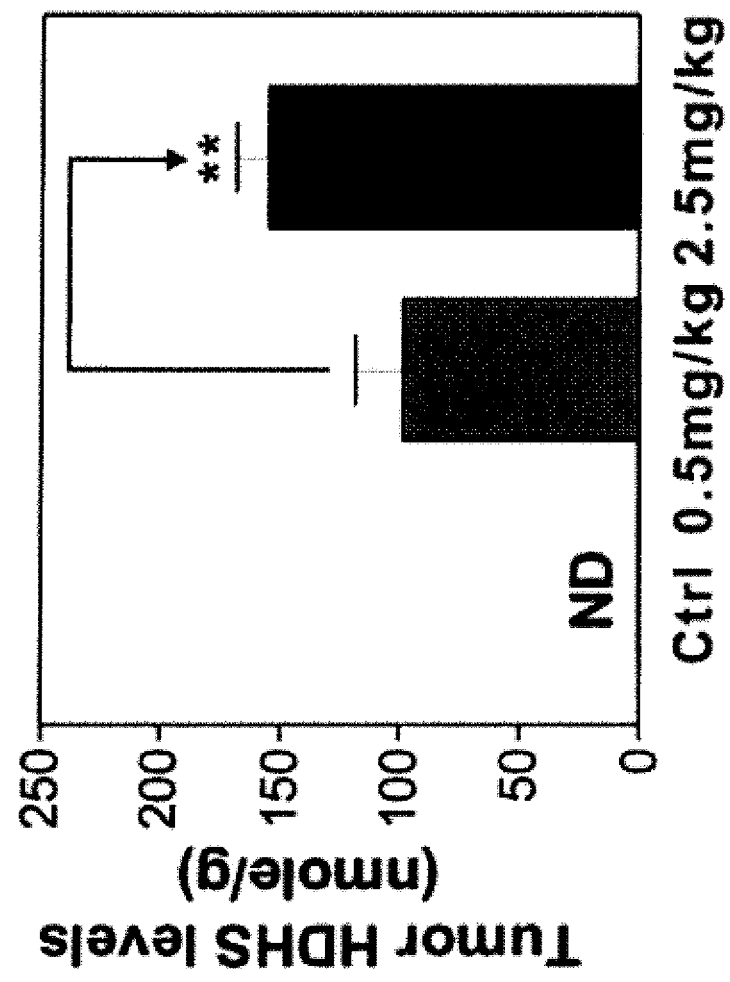
FIG. 10. HDHS levels in tumors.

Oral Intake of HDHS Achieved Effective Concentrations in Plasma and in Tumors in Nude Mice In order to further understand the dose-effect relationships, the attainable levels of HDHS in plasma and tumors were detected 24 h after the last dose of HDHS regimen in the tested mice. As shown in FIG. 7 and FIG. 9, control mice receiving vehicle only showed undetectable levels of HDHS in both plasma and tumors (chromatograms b), whereas HDHS ingestion resulted in sharp dose-dependent peaks in plasma and tumor levels in HPLC profiles (chromatograms c and d). Oral administration of 0.5 and 2.5 mg/kg HDHS resulted in 0.45±0.14 and 1.45±0.30 μM HDHS in plasma (FIG. 8) and accumulated 98.45±19.80 and 154.93±12.97 nmole/g HDHS in tumor tissues (FIG. 10). These increases of HDHS concentrations in plasma and tumors were dose-dependent and consistent with the extent of tumor suppression (FIGS. 6A and B).

What is claimed is:
1. A method of inhibiting androgen receptor activity in a patient comprising administering a diterpene to the patient and allowing the diterpene to reduce androgen receptor activity, wherein the diterpene is chosen from the following compounds:

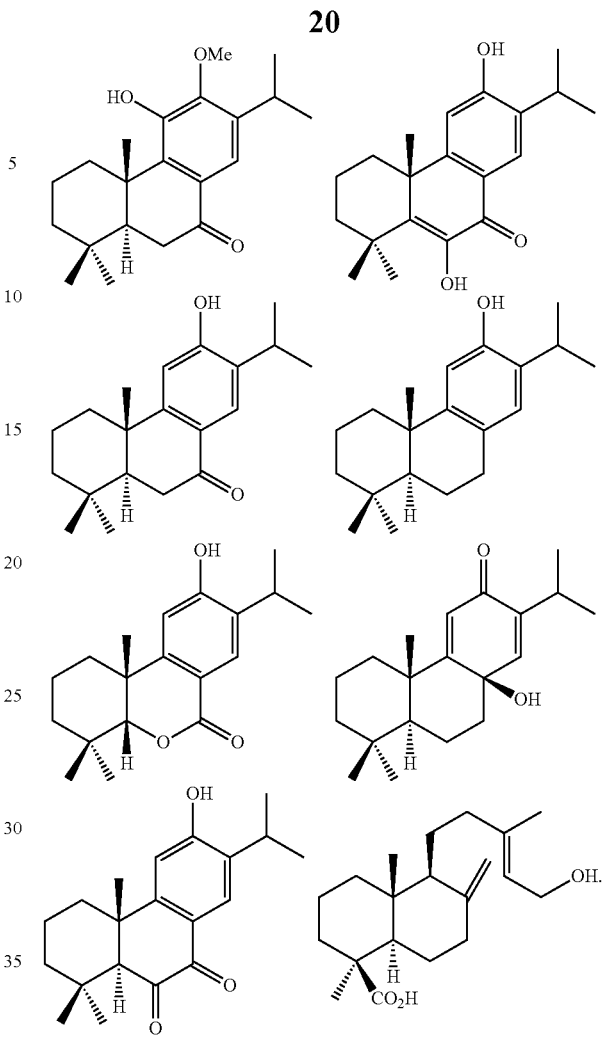

2. The method according to claim 1, wherein the diterpene is:

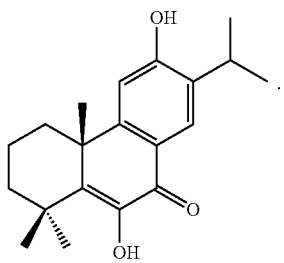

3. The method according to claim 1, wherein the diterpene is:

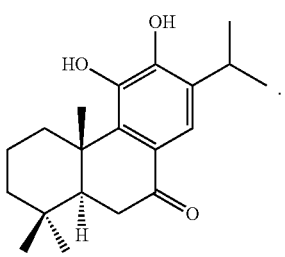

4. The method according to claim 1, wherein the diterpene is:

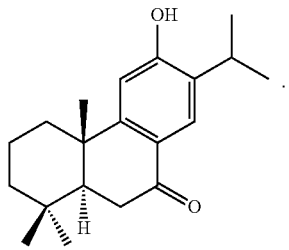

5. The method according to claim 1, wherein the diterpene is:

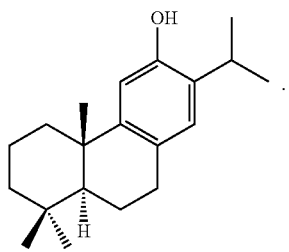

6. The method according to claim 1, wherein the diterpene is:

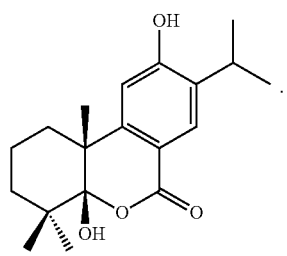

7. The method according to claim 1, wherein the diterpene is:

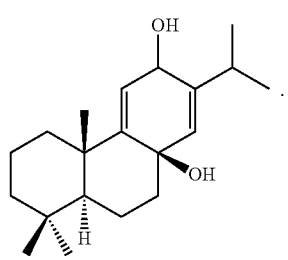

8. The method according to claim 1, wherein the diterpene is:

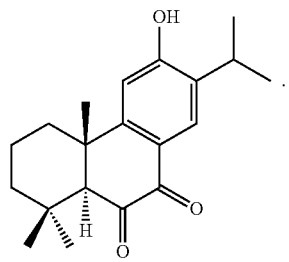

9. The method according to claim 1, wherein the diterpene is:

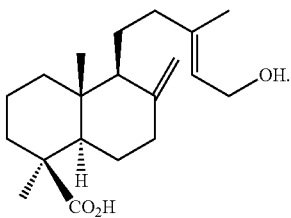 [SMILES: C=C1CC[C@@H]2[C@](C)(CCC[C@]2(C)C(=O)O)[C@H]1CC/C(C)=C/CO]

10. A method of treating an androgen receptor-associated disease comprising administering a diterpene to a patient and allowing the diterpene to reduce androgen receptor activity thereby treating the androgen receptor-associated disease, wherein the diterpene is chosen from the following compounds:

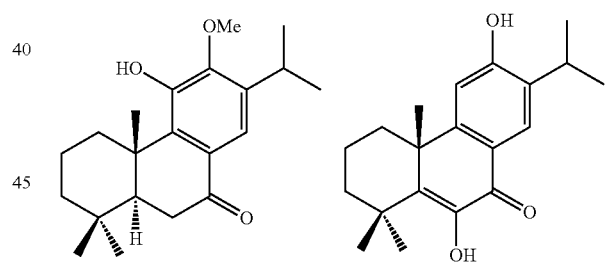

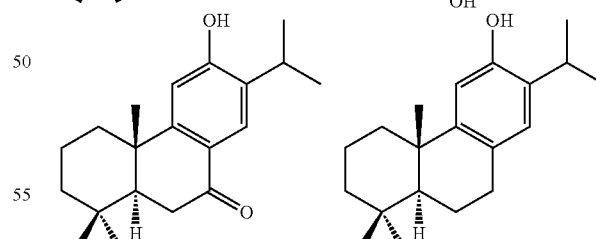

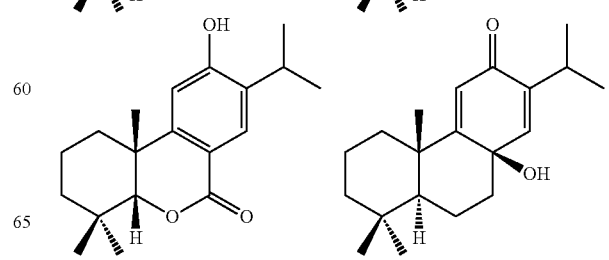

-continued

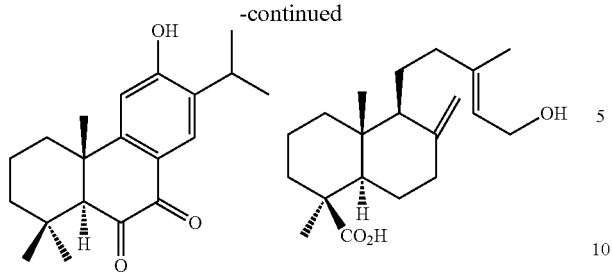

and wherein the androgen receptor-associated disease is chosen from prostate cancer, benign prostate hypertrophy, bladder cancer, breast cancer, polycystic ovary syndrome (PCOS), androgenic alopecia, hirsutism, acne, oily skin, seborrhea, and hidradenitis suppurativar.

11. The method according to claim 10, wherein the androgen receptor-associated disease is prostate cancer.

12. The method according to claim 10, wherein the method further comprises treating the patient with at least one treatment chosen from hormone therapy, chemotherapy, surgery, and irradiation.

* * * * *

UNITED STATES PATENT AND TRADEMARK OFFICE
CERTIFICATE OF CORRECTION

PATENT NO.        : 8,519,007 B2
APPLICATION NO.   : 12/508832
DATED             : August 27, 2013
INVENTOR(S)       : Pei-Wen Hsiao et al.

It is certified that error appears in the above-identified patent and that said Letters Patent is hereby corrected as shown below:

Title page, item (54), and in the Specification, column 1, the title "USE CERTAIN DITERPENE COMPOUNDS IN THE TREATMENT OF ANDROGEN RECEPTOR-ASSOCIATED DISEASES" should read --USE OF CERTAIN DITERPENE COMPOUNDS IN THE TREATMENT OF ANDROGEN RECEPTOR-ASSOCIATED DISEASES--.

In the Claims

Claim 1, col. 20, lines 20-30, left side,

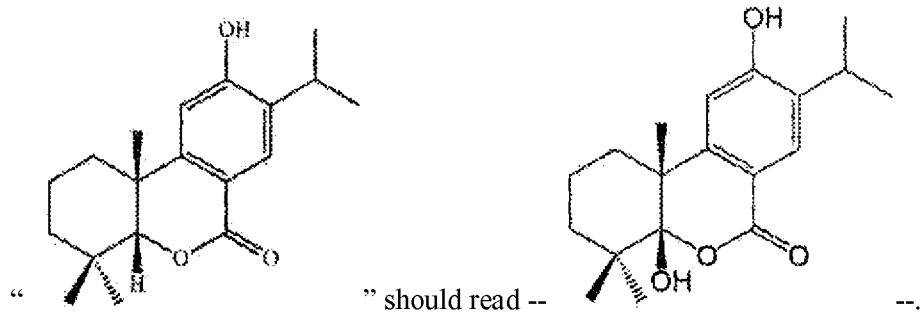

Claim 3, col. 20, lines 57-67,

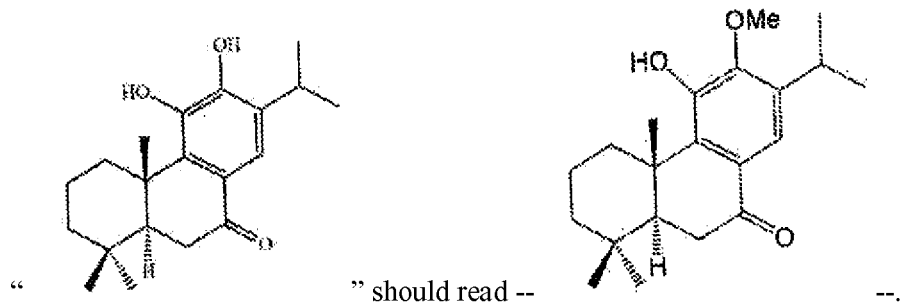

Signed and Sealed this
Seventeenth Day of December, 2013

Margaret A. Focarino
*Commissioner for Patents of the United States Patent and Trademark Office*

CERTIFICATE OF CORRECTION (continued)
U.S. Pat. No. 8,519,007 B2

Claim 7, col. 21, lines 57-67,

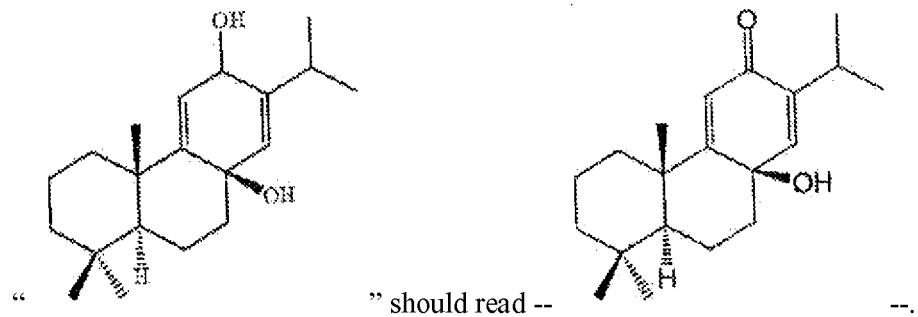

" should read -- --.

Claim 10, col. 22, lines 57-67, left side,

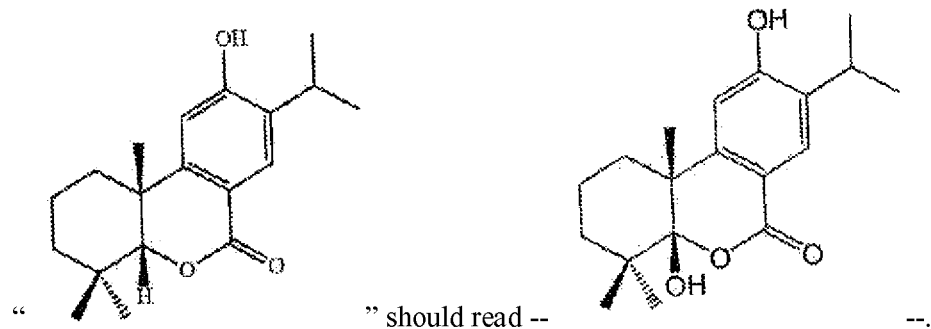

" should read -- --.